(12) United States Patent
Hassan et al.

(10) Patent No.: US 9,532,785 B2
(45) Date of Patent: Jan. 3, 2017

(54) METHOD AND DEVICES FOR FLOW OCCLUSION DURING DEVICE EXCHANGES

(71) Applicant: AccessClosure, Inc., Mountain View, CA (US)

(72) Inventors: Ali Hassan, Palo Alto, CA (US); Kevin To, San Jose, CA (US); Andy H. Uchida, Los Altos, CA (US); Jose Garcia, Fremont, CA (US)

(73) Assignee: Access Closure, Inc., Santa Clara, CA (US)

( * ) Notice: Subject to any disclaimer, the term of this patent is extended or adjusted under 35 U.S.C. 154(b) by 155 days.

(21) Appl. No.: 13/889,842

(22) Filed: May 8, 2013

(65) Prior Publication Data

US 2013/0304107 A1 Nov. 14, 2013

Related U.S. Application Data

(60) Provisional application No. 61/644,868, filed on May 9, 2012.

(51) Int. Cl.
*A61F 2/06* (2013.01)
*A61B 17/12* (2006.01)

(52) U.S. Cl.
CPC ..... *A61B 17/12136* (2013.01); *A61B 17/1204* (2013.01); *A61B 17/12031* (2013.01); *A61B 17/12109* (2013.01)

(58) Field of Classification Search
CPC ............ A61F 2/07; A61F 2/954; A61F 2/958; A61B 17/12136; A61B 17/12031; A61B 17/1204; A61B 17/12109
See application file for complete search history.

(56) References Cited

U.S. PATENT DOCUMENTS

| 4,846,174 A | 7/1989 | Willard et al. |
| 4,886,067 A | 12/1989 | Palermo |
| 4,998,923 A | 3/1991 | Samson et al. |

(Continued)

FOREIGN PATENT DOCUMENTS

| WO | 9826833 A1 | 6/1998 |
| WO | WO 2008/048568 | 4/2008 |

(Continued)

OTHER PUBLICATIONS

International Search Report and Written Opinion for PCT/US2012/043832 mailed Sep. 24, 2012, in 20 pages.

(Continued)

*Primary Examiner* — Ashley Fishback
(74) *Attorney, Agent, or Firm* — Amanda F. Maharaj

(57) ABSTRACT

Methods and devices for maintaining vascular access and/or minimizing bleeding during percutaneous interventions. The method can include advancing an access wire through a previously placed access catheter in a contralateral femoral artery to position an inflatable balloon on the access wire in a vascular access sheath located in an ipsilateral femoral artery, without using any additional guidewires to advance the access wire. After withdrawing the vascular access sheath at least partway out of the ipsilateral femoral artery to expose the vascular injury, the balloon can be inflated to occlude the ipsilateral femoral artery or an ipsilateral iliofemoral artery at or near the vascular injury.

13 Claims, 28 Drawing Sheets

(56) References Cited

U.S. PATENT DOCUMENTS

| | | |
|---|---|---|
| 5,125,895 A | 6/1992 | Buchbinder et al. |
| 5,167,239 A | 12/1992 | Cohen et al. |
| 5,169,386 A | 12/1992 | Becker et al. |
| 5,207,229 A | 5/1993 | Winters |
| 5,209,727 A * | 5/1993 | Radisch, Jr. .......... A61M 25/09 604/913 |
| 5,234,003 A | 8/1993 | Hall |
| 5,263,931 A | 11/1993 | Miller |
| 5,338,301 A | 8/1994 | Diaz |
| 5,370,685 A | 12/1994 | Stevens |
| 5,484,409 A | 1/1996 | Atkinson et al. |
| 5,520,645 A | 5/1996 | Imran et al. |
| 5,527,292 A | 6/1996 | Adams et al. |
| 5,609,627 A | 3/1997 | Goicoechea et al. |
| 5,779,688 A | 7/1998 | Imran et al. |
| 5,807,318 A | 9/1998 | St. Goar et al. |
| 6,090,083 A | 7/2000 | Sell et al. |
| 6,235,050 B1 * | 5/2001 | Quiachon et al. ........... 623/1.11 |
| 6,302,898 B1 | 10/2001 | Edwards et al. |
| 6,322,577 B1 | 11/2001 | Mcinnes |
| 6,325,777 B1 | 12/2001 | Zadno-Azizi et al. |
| 6,451,043 B1 | 9/2002 | Mcinnes et al. |
| 6,602,207 B1 | 8/2003 | Mam et al. |
| 6,786,888 B1 | 9/2004 | Zadno-Azizi et al. |
| 6,923,822 B2 | 8/2005 | Crawford et al. |
| 7,063,714 B2 | 6/2006 | Dorros et al. |
| 7,169,161 B2 | 1/2007 | Bonnette et al. |
| 7,316,704 B2 | 1/2008 | Bagaoisan et al. |
| 7,331,979 B2 | 2/2008 | Khosravi et al. |
| 7,335,220 B2 | 2/2008 | Khosravi et al. |
| 7,713,227 B2 | 5/2010 | Wholey et al. |
| 7,806,856 B2 | 10/2010 | Bagaoisan et al. |
| 7,993,367 B2 | 8/2011 | Bagaoisan et al. |
| 8,029,533 B2 | 10/2011 | Bagaoisan et al. |
| 8,038,672 B2 | 10/2011 | Malecki et al. |
| 8,157,766 B2 | 4/2012 | Bonnette et al. |
| 8,394,122 B2 | 3/2013 | Bagaoisan et al. |
| 8,491,648 B2 | 7/2013 | Hassan et al. |
| 8,617,204 B2 | 12/2013 | Khosravi et al. |
| 8,795,709 B2 | 8/2014 | Sawhney et al. |
| 8,852,230 B2 | 10/2014 | Sawhney et al. |
| 2002/0072730 A1 | 6/2002 | McGill et al. |
| 2002/0173817 A1 | 11/2002 | Kletschka et al. |
| 2002/0198594 A1 * | 12/2002 | Schreck ................ 623/2.11 |
| 2003/0060802 A1 | 3/2003 | Omaleki et al. |
| 2004/0249342 A1 | 12/2004 | Khosravi et al. |
| 2005/0033346 A1 | 2/2005 | Sater |
| 2005/0124939 A1 | 6/2005 | Konstantino |
| 2005/0182437 A1 | 8/2005 | Bonnette et al. |
| 2006/0217755 A1 | 9/2006 | Eversull et al. |
| 2006/0258987 A1 | 11/2006 | Lentz et al. |
| 2007/0083187 A1 | 4/2007 | Eversull et al. |
| 2007/0167876 A1 | 7/2007 | Euteneuer et al. |
| 2007/0231366 A1 | 10/2007 | Sawhney et al. |
| 2008/0082122 A1 | 4/2008 | Khosravi et al. |
| 2008/0172118 A1 | 7/2008 | Johnson et al. |
| 2009/0030409 A1 | 1/2009 | Goldfarb et al. |
| 2009/0088793 A1 | 4/2009 | Bagaoisan et al. |
| 2009/0254110 A1 | 10/2009 | Bagaoisan et al. |
| 2009/0318798 A1 | 12/2009 | Singh et al. |
| 2010/0159117 A1 | 6/2010 | Griffin et al. |
| 2010/0168789 A1 | 7/2010 | Bagaoisan et al. |
| 2010/0274085 A1 | 10/2010 | Mugan et al. |
| 2010/0274280 A1 | 10/2010 | Sawhney et al. |
| 2010/0280546 A1 | 11/2010 | Campbell et al. |
| 2011/0009888 A1 | 1/2011 | Shturman |
| 2011/0118759 A1 | 5/2011 | Teichman et al. |
| 2011/0319922 A1 | 12/2011 | Kitagawa |
| 2013/0046376 A1 | 2/2013 | Hassan et al. |
| 2013/0060318 A1 | 3/2013 | Hassan et al. |

FOREIGN PATENT DOCUMENTS

| | | |
|---|---|---|
| WO | WO 2009/086512 | 7/2009 |
| WO | WO 2012/178073 | 12/2012 |

OTHER PUBLICATIONS

Notice of Allowance in U.S. Appl. No. 13/668,585 dated May 1, 2013, in 12 pages.

Office Action in U.S. Appl. No. 13/531,227 dated May 1, 2013, in 5 pages.

Office Action in U.S. Appl. No. 13/668,585 dated Feb. 15, 2013, in 5 pages.

Scheinert, et al. Treatment of Catheter-Induced Iliac Artery Injuries With Self-Expanding Endografts. J Endovasc Ther. Jun. 2000; 7: 213-220.

Yamagami, et al. A Case of Iatrogenic Subclavian Artery Injury Successfully Treated with Endovascular Procedures. Annals of Vascular Diseases. Mar. 2011; 4(1): 53-55.

Extended European Search Report for EP application 12801817.3 mailed Feb. 2, 2015, 6 pages.

Office Action in U.S. Appl. No. 13/531,227 dated Jul. 29, 2013, 17 pages.

Office Action in U.S. Appl. No. 13/531,227 dated Jul. 17, 2014, 31 pages.

Office Action in U.S. ApplNo. 13/531,227 dated Mar. 12, 2015, 39 pages.

International Preliminary Report on Patentability and Written Opinion for PCT/US2012/043832 mailed Dec. 24, 2013, in 9 pages Non-Final Office Action mailed Aug. 27, 2015 for U.S. Appl. No. 13/531,227, filed Jun. 22, 2012.

Extended European Search Report for Application No. EP13845971, mailed on May 10, 2016, 8 pages.

International Search Report and Written Opinion for Application No. PCT/US2015/060516, mailed on Feb. 18, 2016, 13 pages.

International Search Report for Application No. PCT/US2013/063725, mailed on Jan. 3, 2014, 8 pages.

Office Action in corresponding Chinese Patent Application No. 2013-80052855 dated Apr. 5, 2016.

\* cited by examiner

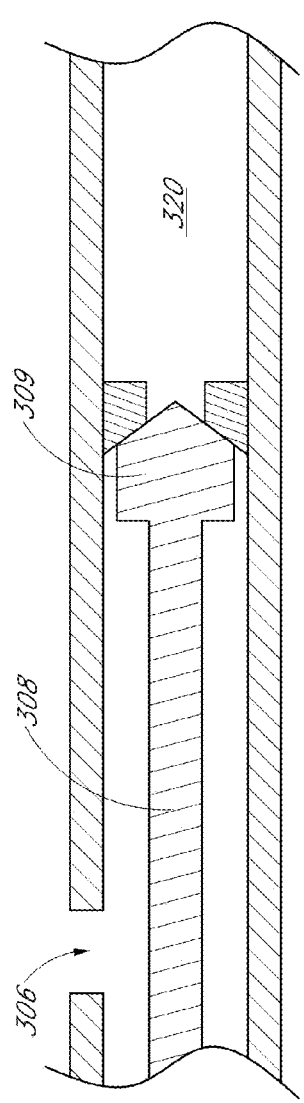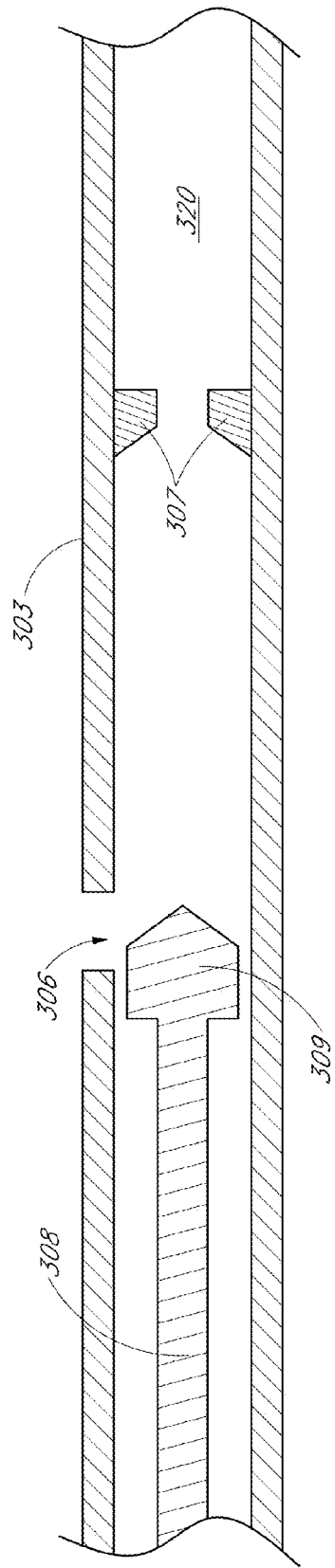
FIG. 4A
FIG. 4B

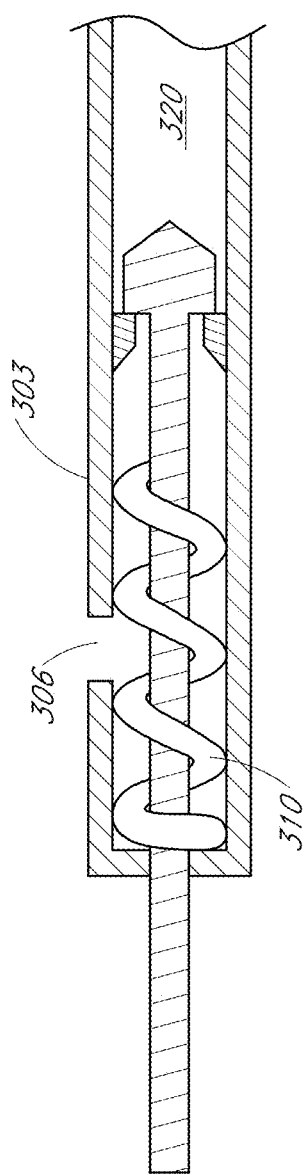
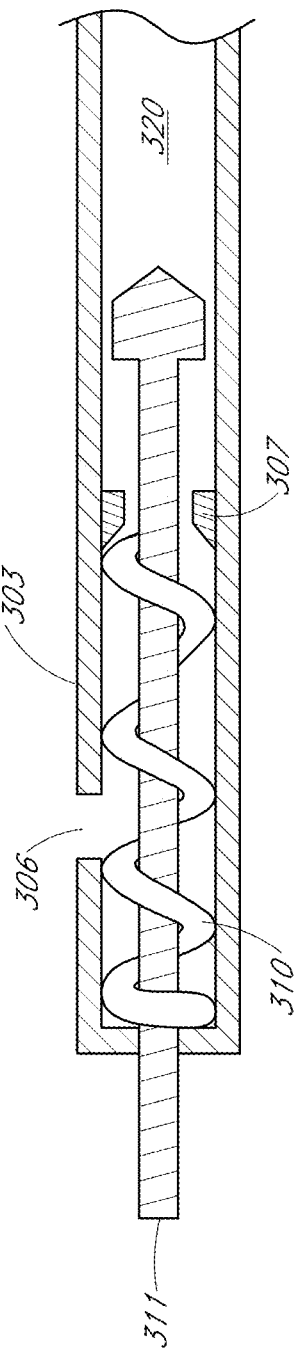
FIG. 5A
FIG. 5B

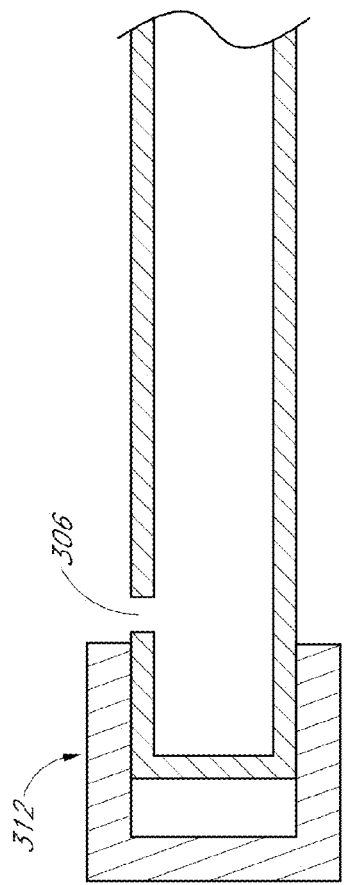
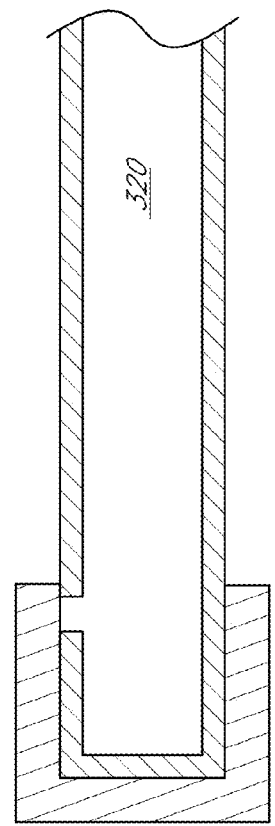
FIG. 6A
FIG. 6B

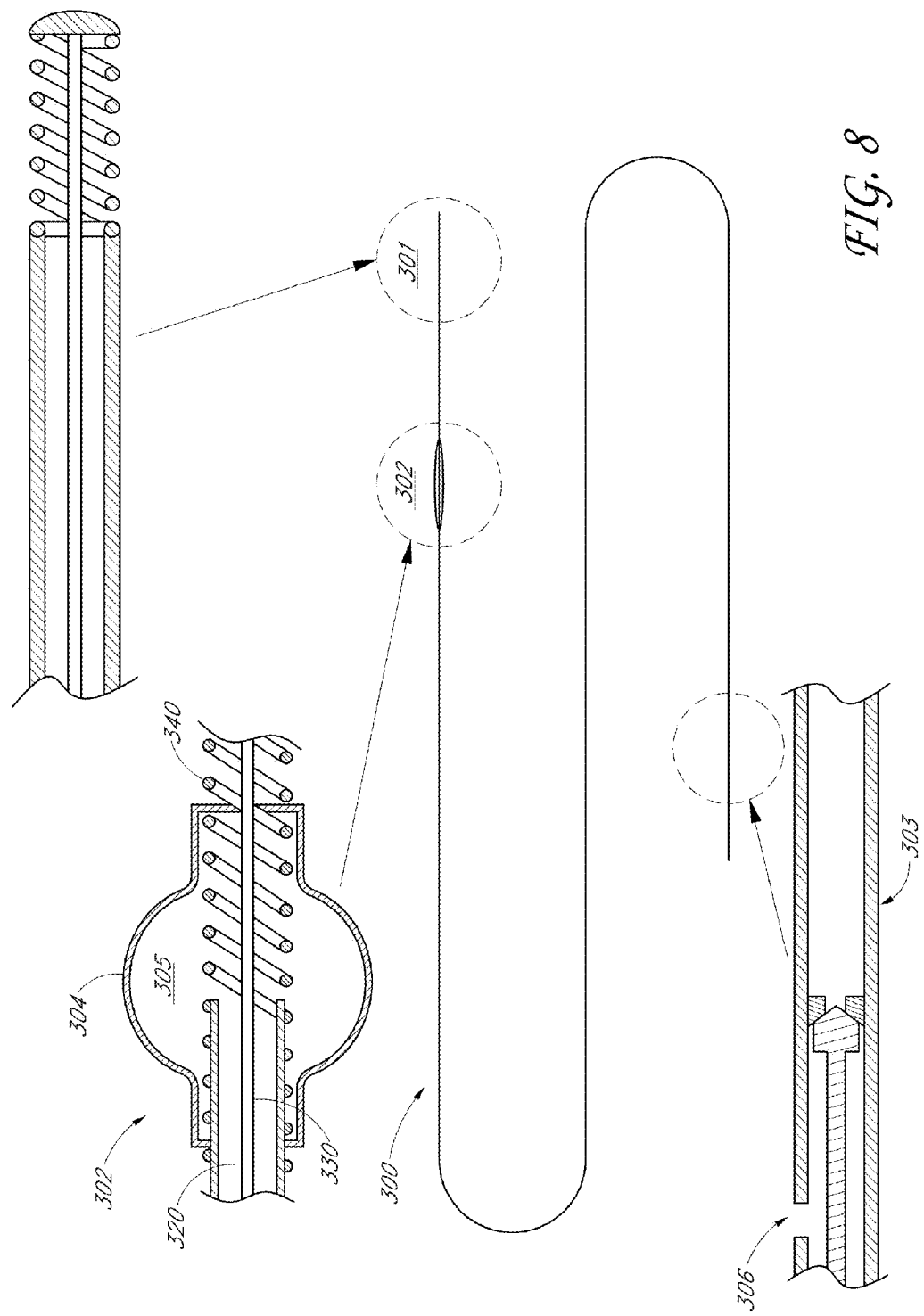

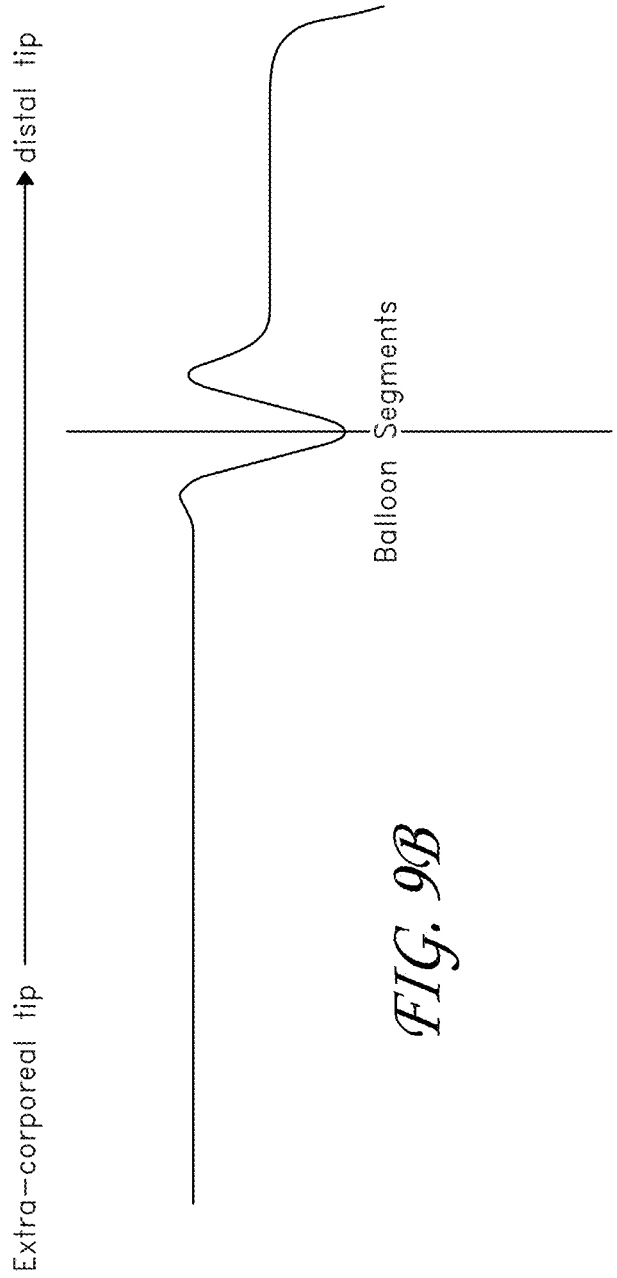

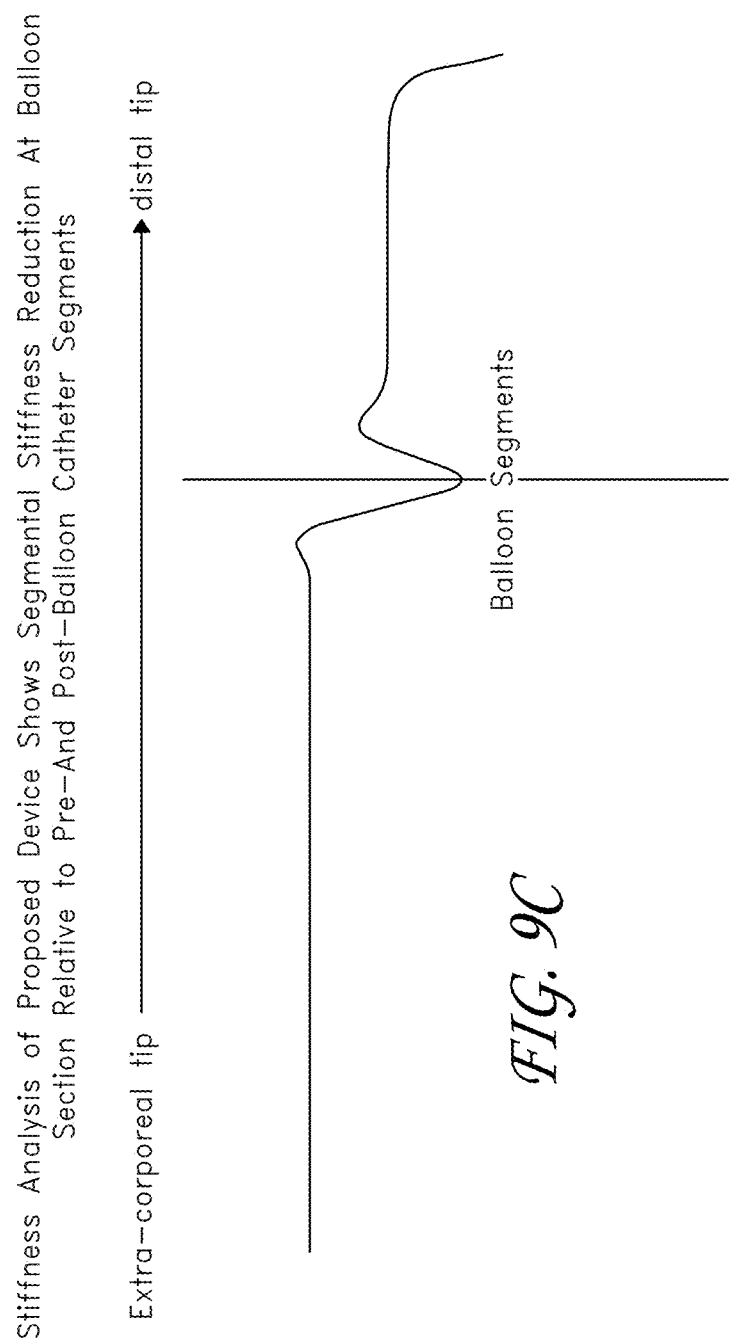

J-tip positioning in aorta      Occlusive position at arteriotomy

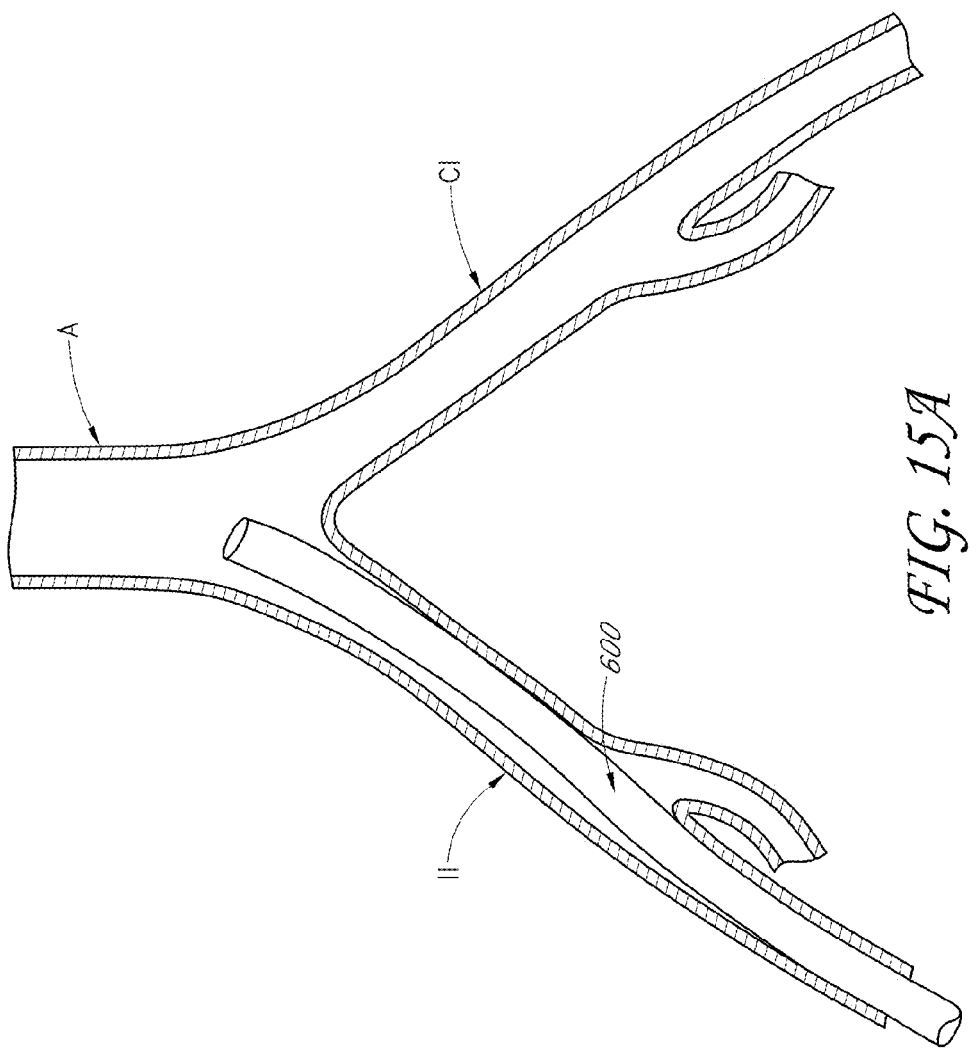

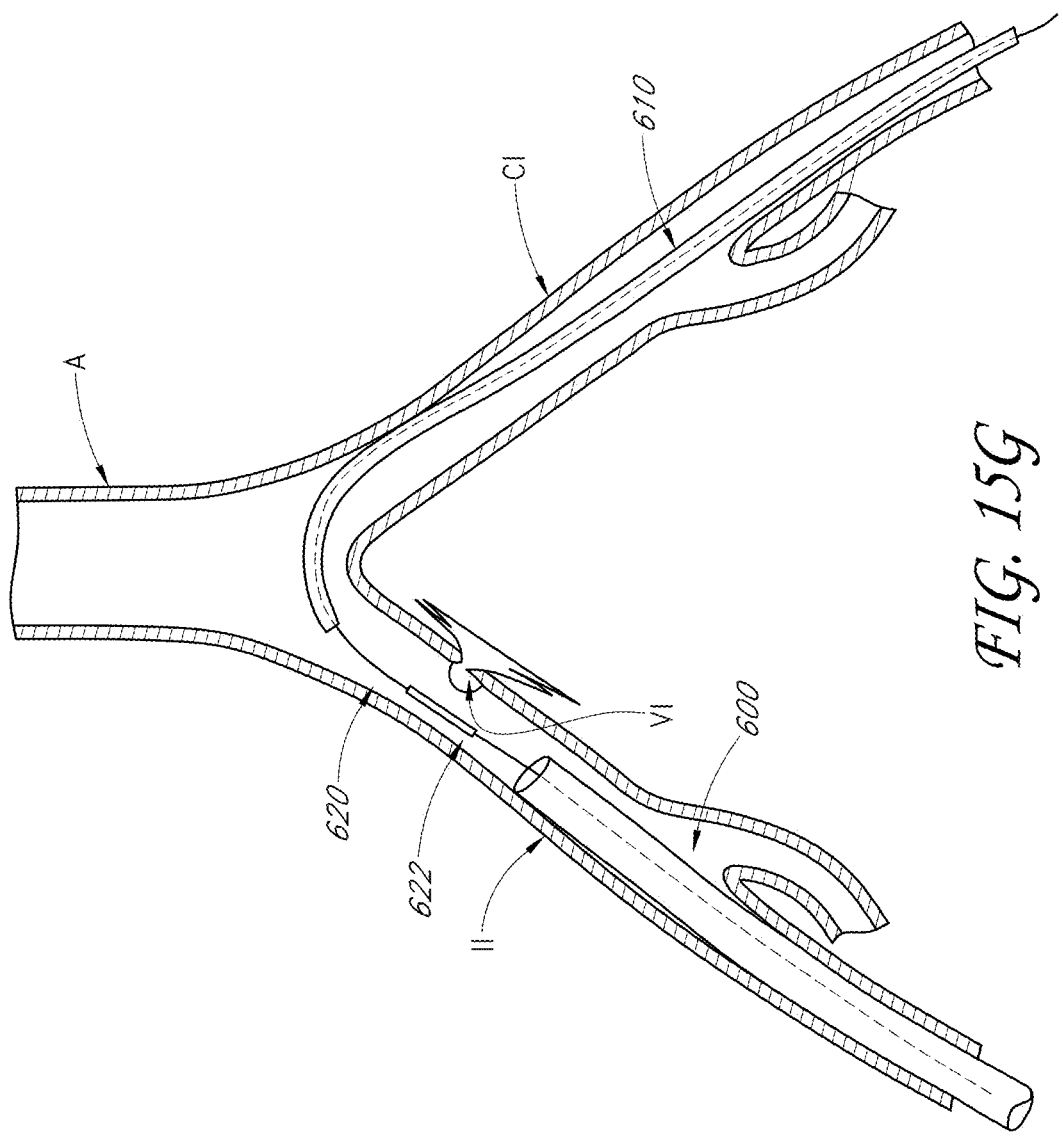

METHOD AND DEVICES FOR FLOW OCCLUSION DURING DEVICE EXCHANGES

CROSS-REFERENCE TO RELATED APPLICATIONS

This application claims the benefit of priority under 35 U.S.C. §119(e) of U.S. Provisional Patent Application No. 61/644,868, filed May 9, 2012, which is hereby incorporated herein by reference in its entirety.

BACKGROUND

Field

The field of the present application pertains to medical devices, and more particularly, to methods and systems for maintaining vascular access and/or minimizing bleeding, for example, during and after catheter-based interventions, for example, in the settings of device exchanges, vascular access closure, and the management of vascular complications.

Description of the Related Art

Catheter-based medical procedures using large diameter (or "large bore") vascular access sheaths are becoming increasingly more common. Two examples of such large bore catheterization procedures that are gaining rapid popularity are Transcatheter Aortic Valve Implantation ("TAVI") and EndoVascular abdominal Aortic aneurysm Repair ("EVAR"). Although these procedures may often be effective at treating the condition addressed, they often cause injury to the blood vessel in which the large bore vascular access catheter is inserted to gain access for performing the procedure. In fact, vascular injury requiring treatment occurs in as many as 40% of large bore vascular procedures, according to some sources. Injury to the blood vessel may include perforation, rupture and/or dissection, which causes blood to flow out of the artery ("extravascular bleeding"), often requiring emergency surgery to repair the damaged blood vessel wall. If not properly treated, such a vascular injury may lead to anemia, hypotension or even death.

Vascular injury during large bore intravascular procedures is typically caused by the vascular access sheath itself and/or one or more instruments passed through the sheath to perform the procedure. Larger diameter vascular access sheaths are required in a number of catheter-based procedures, such as those mentioned above, where relatively large catheters/instruments must be passed through the sheath. Several other factors may increase the risk of vascular injury, including occlusive disease of the access vessel(s) and tortuosity/angulation of the access vessel(s). Another vascular injury caused by large bore intravascular procedures that can be challenging is the access site itself. Typically, large bore catheterizations create a significantly large arteriotomy, due to a disproportionately large ratio of the diameter of the vascular access catheter to the diameter of the artery in which it is placed. Large arteriotomies may require special management and multiple steps during closure. This may lead to significant blood loss while access closure is attempted.

Several techniques have been attempted to reduce the incidence of vascular injury in large bore vascular access procedures. For example, preoperative imaging of the blood vessel to be accessed, in the form of CT and MR angiography, may provide the physician with an idea of the anatomy of the vessel. If a particular vessel appears on imaging studies to be relatively tortuous or small, possible adjunctive maneuvers to prevent arterial dissection include pre-dilatation angioplasty of the iliofemoral vessels prior to large bore sheath placement, utilization of smaller access sheaths when possible, stiffer wires to aid in sheath placement and/or use of hydrophobic sheaths. In another attempt at preventing vessel injury, sheath placement may be performed under fluoroscopic guidance, and advancement may be halted when resistance is encountered. Despite the availability of these techniques, vascular injury requiring treatment still occurs in a large percentage of large bore vascular procedures.

Vascular injuries caused by intravascular procedures are generally quite difficult to diagnose and treat. When an arterial dissection occurs, it often remains undetected until the catheterization procedure is completed and the vascular access sheath is removed. For example, upon removal of the access sheath, large segments of the dissected vessel wall may be released within the vessel. The dissected vessel wall may lead to a breach in the artery wall, a flow-limiting stenosis, or distal embolization. Perforation or rupture of the iliofemoral artery segment may occur from persistent attempts to place large access sheaths in iliac arteries that are too small, too diseased, and/or too tortuous. Here too, a perforation may be likely to remain silent until sheath withdrawal.

Adding to the difficulties presented by vascular injuries caused by large bore procedures, diagnosis of catheter-induced iliofemoral injuries is often difficult. Upon sheath withdrawal, contrast injections may reveal beginning dissections as lumen irregularities. Unfortunately, however, due to the deep location of most of the iliofemoral arterial segment, transcutaneous ultrasound imaging does not always yield interpretable results. Doppler ultrasound of the distal flow bed, however, may be used to diagnose an upstream flow-limiting entity. For example, after closure of the access site, if the inflow into the limb is poor or the Doppler signals in the extremity are diminished in comparison to the preoperative examination, an arterial dissection/perforation should be considered. An arteriogram may be indicated for any abnormal vascular examination findings to delineate the underlying anatomy.

Generally, vascular perforations and dissections caused by large bore vascular procedures allow very little time for the interventionalist to react. Frequently, these vascular injuries are associated with serious clinical sequelae, such as massive internal (retroperitoneal) bleeding, abrupt vessel closure, vital organ injuries, and emergency surgeries. In some cases, an interventionalist may first attempt to repair a vascular injury using an endovascular approach. First, the injury site may be controlled/stabilized with a balloon catheter, in an attempt to seal off the breached vessel wall and/or regain hemodynamic stability in the presence of appropriate resuscitation and transfusion of the patient by the anesthesiologist. Subsequently, endovascular treatment solutions may be attempted, for example if wire access is maintained through the true lumen. This may involve placement of one or more balloons, stents, or covered stents across the dissection/perforation. If the hemorrhage is controlled with these maneuvers and the patient is hemodynamically stabilized, significant reduction in morbidity and mortality may be realized. If attempts at endovascular repair of the vessel fail, emergency surgery is typically performed.

Presently, vascular injuries and complications occurring during and after large bore intravascular procedures are managed using a contralateral balloon occlusion technique ("CBOT"). CBOT involves accessing the contralateral femoral artery (the femoral artery opposite the one in which the large bore vascular access sheath is placed) with a separate access sheath, and then advancing and maneuvering a series of different guidewires, sheaths and catheters into the injured (ipsilateral) femoral or iliofemoral artery to treat the injury. Eventually, a (pre-sized) standard balloon catheter is advanced into the injured artery, and the balloon is inflated to reduce blood flow into the area of injury, thus stabilizing the injury until a repair procedure can be performed. Typically, CBOT involves at least the following steps: (1) Place a catheter within the contralateral iliofemoral artery (this catheter may already be in place for use in injecting contrast during the intravascular procedure); (2) Advance a thin, hydrophilic guidewire through the catheter and into the vascular access sheath located in the ipsilateral iliofemoral artery; (3) Remove the first catheter from the contralateral iliofemoral artery; (4) Advance a second, longer catheter over the guidewire and into the vascular access sheath; (5) Remove the thin, hydrophilic guidewire; (6) Advance a second, stiffer guidewire through the catheter into the vascular access sheath; (7) In some cases, an addition step at this point may involve increasing the size of the arteriotomy on the contralateral side to accommodate one or more balloon catheter and/or treatment devices for treating arterial trauma on the ipsilateral side; (8) Advance a balloon catheter over the stiffer guidewire into the damaged artery; (9) Inflate the balloon on the catheter to occlude the artery; (10) Advance one or more treatment devices, such as a stent delivery device, to the site of injury and repair the injury.

As this description suggests, the current CBOT technique requires many steps and exchanges of guidewire and catheters, most of which need to be carefully guided into a vascular access catheter in the opposite (ipsilateral) iliofemoral artery. Thus, the procedure is quite challenging and cumbersome. Although considered the standard of care in the management of vascular complications, the CBOT technique may not provide immediate stabilization of an injured segment, may lack ipsilateral device control, and/or may not provide ready access for additional therapeutics such as stents, other balloons and the like.

Therefore, in the management of vascular injuries and complications stemming from large bore intravascular procedures, it would be useful to provide a solution for minimizing blood loss and bridging the time to treatment (for example, an endovascular or surgical procedure) while maintaining an access pathway for delivering one or more treatment devices (balloon catheters, stents, etc.) to the injury site. It would also be desirable to provide blood flow occlusion during vascular closure after femoral artery catheterization. Ideally, a device for blood flow occlusion would be compatible with commonly available blood vessel closure devices and techniques, to facilitate blood flow occlusion during closure and occlusion device removal after closure. At least some of these objectives will be met by the embodiments described herein.

SUMMARY

Example embodiments described herein have several features, no single one of which is indispensable or solely responsible for their desirable attributes. Without limiting the scope of the claims, some of the advantageous features of some embodiments will now be summarized.

The present application is directed generally to medical devices, and more particularly, to methods and devices for maintaining vascular access and/or minimizing bleeding during percutaneous interventions.

For example, the methods and devices described herein may allow for simultaneous blood flow occlusion and device exchanges in the iliofemoral segment. In addition or alternatively, the methods and devices may maintain percutaneous vascular access while allowing for simultaneous flow occlusion and device exchanges. Optionally, the methods and devices may be utilized through the same (ipsilateral) interventional access site. The methods and devices may also be compatible with commonly available balloon/stent, and/or vascular closure systems.

In one aspect of the present invention, a method of treating a vascular injury occurring during or after an intravascular procedure may involve: advancing an access wire through a previously placed access catheter in a contralateral femoral artery to position an inflatable balloon on the access wire in a vascular access sheath located in an ipsilateral femoral artery, without using any additional guidewires to advance the access wire; withdrawing the vascular access sheath at least partway out of the ipsilateral femoral artery to expose the vascular injury; inflating the balloon to occlude the ipsilateral femoral artery or an ipsilateral iliofemoral artery at or near the vascular injury; removing an inflation device from a proximal portion of the access wire, wherein a proximal end of the access wire is hubless, and wherein the balloon remains inflated after inflation device removal; advancing at least one treatment device over the hubless proximal end of the access wire; and treating the vascular injury using the at least one treatment device.

In some embodiments, the access catheter may be placed in the contralateral femoral artery before or during the intravascular procedure to provide contrast dye or other instruments during the procedure. In alternative embodiments, the access catheter may be a curved catheter with a curved in a distal portion for navigating around the aortic bifurcation, and the method may further involve advancing this catheter into the contralateral femoral artery. In some embodiments, advancing the access wire may involve advancing through the contralateral iliofemoral artery, through the aorta and into the ipsilateral iliofemoral artery. In some embodiments, the access wire may have sufficient stiffness to straighten the aorta slightly at an area of bifurcation of the aorta into two iliac arteries. The balloon of the access wire may help maintain the access wire within the ipsilateral iliofemoral artery, once it is advanced into it, by preventing the access wire from flicking out of the artery, as might happen with a stiff wire without a balloon.

In some embodiments, the method may further involve, before inflating the balloon, injecting contrast into the ipsilateral artery, and observing the contrast using a radiographic imaging device to evaluate whether the vascular injury exists. In some embodiments, inflating the balloon may involve inflating at a location of the vascular injury. In some embodiments, inflating the balloon may involve inflating at a location upstream of the vascular injury. In some embodiments, the treatment device may include a stent deployment catheter, and treating the vascular injury may involve placing a stent in the blood vessel. In some embodiments, the intravascular procedure may involve implantation of an aortic valve. In alternative embodiments, the intravascular procedure may involve an abdominal aortic aneurysm repair.

In another aspect of the present invention, a method of treating a vascular injury occurring during or after an intravascular procedure may involve: advancing an access wire through a previously placed access catheter in a first iliofemoral artery to position an inflatable balloon on the access wire in a vascular access sheath located in a second iliofemoral artery, without using any additional guidewires or catheters other than the access catheter to advance the access wire; locating the vascular injury in the second iliofemoral artery; inflating the balloon to occlude the second iliofemoral artery at or near the vascular injury; advancing at least one treatment device over the hubless proximal end of the access wire; and treating the vascular injury using the at least one treatment device.

In another aspect of the present invention, a method of treating a vascular injury occurring during or after an intravascular procedure may involve: advancing an access wire through a previously placed access catheter in a first femoral artery to position an inflatable balloon on the access wire in a vascular access sheath located in a second femoral artery, without using any additional guidewires to advance the access wire; withdrawing the vascular access sheath at least partway out of the second femoral artery to expose the vascular injury; inflating the balloon within the vascular access sheath to anchor the access wire relative to the sheath; advancing at least one treatment device over a hubless proximal end of the access wire; and treating the vascular injury using the at least one treatment device.

In another aspect of the present invention, an access wire balloon device for occluding a blood vessel and providing a wire over which to advance one or more treatment devices in a blood vessel which has sustained an injury from a catheter based intravascular procedure may include an elongate flexible tubular body having a hubless proximal end, a distal end and a central lumen, where the elongate body has a first section starting at the proximal end, which is more stiff than any other section of the tubular body, a second section extending from a distal end of the first section and becoming increasingly flexible along its length from proximal to distal, a third section having a relatively constant flexibility along its length, where the relatively constant flexibility is greater than a flexibility of a most flexible portion of the second section, and a fourth section extending from a distal end of the third section to the distal end of the tubular body that is substantially more flexible than any other section of the body. The access wire balloon device may also include: an inflatable balloon disposed along the tubular body between the second and third sections and in communication with the lumen; and a locking valve on the first section of the elongate body configured to couple with an inflation device to allow for inflation and deflation of the balloon and to lock to maintain the balloon in an inflated configuration when the inflation device is removed and thus allow one or more additional devices to be passed over the proximal end of the elongate body while the balloon remains inflated.

In some embodiments, the valve may include an axially movable occluder, positioned within the lumen. In these embodiments, the occluder may be movable between a proximal position and a distal position, and the valve is closed when the occluder is in the distal position. In some embodiments, the third and fourth sections may have a total length of no more than about 5 cm. In some embodiments, the third and fourth sections may have a substantially straight configuration when unconstrained. Some embodiments may further include a fifth section disposed between the second and third sections, where the balloon is disposed on the fifth section, and where the fifth section has a flexibility greater than or equal to the flexibility of the most flexible portion of the second section.

In some embodiments, the first and second sections include a hypotube, and the second section comprises a spiral cut in the hypotube with decreasing spacing in the spiral cut toward a distal end of the second section. In some embodiments, the third section includes a core wire wrapped in a coil, and the core wire extends through the fifth section and into the second section and is attached to an inner wall of the second section. Some embodiments may further include a coating over the spiral cut to prevent fluid from passing out of the lumen through the cut.

In another aspect of the present invention, an access wire balloon system for occluding a blood vessel and providing a wire over which to advance one or more treatment devices in a blood vessel which has sustained an injury from a catheter based intravascular procedure may include an access wire balloon device, including an elongate, flexible tubular body having a hubless proximal end, a distal end and a central lumen, the elongate body having a flexibility profile from the proximal end to the distal end comprising: a first section starting at the proximal end and having the greatest stiffness of any section of the elongate body; a second section more flexible than the first section and having a continuously increasing flexibility; and a third section more flexible than the second section and having a relatively constant flexibility. The access wire balloon device may further include: an inflatable balloon disposed along the tubular body nearer the distal end than the proximal and in communication with the lumen; and a locking valve on the first section of the elongate body configured to allow for inflation and deflation of the balloon and to lock to maintain the balloon in an inflated configuration and thus allow one or more additional devices to be passed over the proximal end of the elongate body while the balloon remains inflated. Finally, the system may further include an inflation device removably attachable with the first section of the elongate body and configured to inflate and deflate the balloon and lock and unlock the locking valve.

In some embodiments, the elongate body may further include a fourth section extending from a distal end of the third section to the distal end of the elongate body, where the fourth section is more flexible than any other section. In some embodiments, the third and fourth sections may have an approximately straight configuration when not constrained. In some embodiments, the elongate body may have an overall stiffness sufficient to allow it to be advanced through a first iliofemoral artery and an aorta into a second iliofemoral artery without the use of any additional guidewire. In some embodiments, the elongate body may have an overall length sufficient to allow it to be advanced through a first iliofemoral artery and an aorta into a second iliofemoral artery to position the balloon in the second iliofemoral artery while the locking valve resides outside a leg of a human in which the first iliofemoral artery resides.

Optionally, some embodiments of the system may further include a syringe removably attachable to the inflation device to inflate the balloon. Also optionally, some embodiments of the system may further include an access catheter for facilitating advancement of the access wire balloon device into an iliofemoral artery.

These and other aspects and embodiments of the invention will be described below in further detail, in relation to the attached drawings.

BRIEF DESCRIPTION OF THE DRAWINGS

FIGS. 4A-7B show alternative embodiments of fluid regulator/valve systems that may be included in an access wire device, such as that shown in FIG. 3.

FIG. 8 shows one embodiment of the inflatable segment.

FIGS. 9A-9E illustrate alternative stiffness characteristics of the individual segments of the access wire device.

FIGS. 15A-15K illustrate a method of limiting clinical sequelae of a vascular injury via a contralateral approach, according to one embodiment of the present invention.

DETAILED DESCRIPTION

Although certain embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Figure 1A:
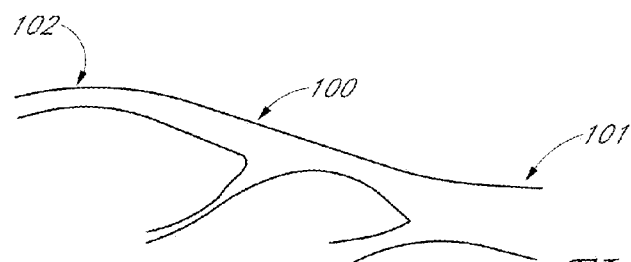
FIGS. 1A-1E show an exemplary method for controlling blood flow during access closure.
Figure 1B:
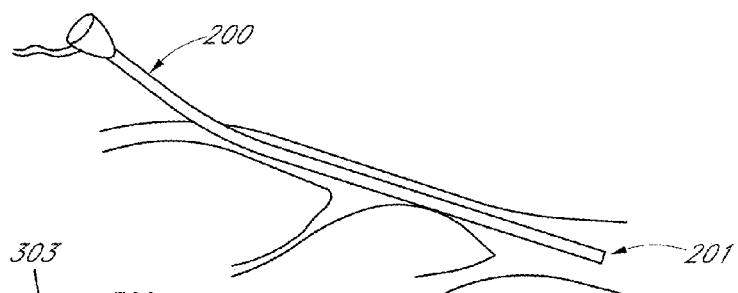

Referring now to FIGS. 1A-1E, one embodiment of a method for controlling bleeding during vascular closure, for example after femoral artery catheterization, is illustrated. FIG. 1A shows a segment of an arterial pathway, including the iliofemoral artery 100, the femoral artery 102, and the aorta 101. FIG. 1B shows a vascular sheath 200 inserted through a vascular access site in the femoral artery 102 and extending through the iliofemoral segment 100 for conducting any suitable diagnostic and/or therapeutic catheterization procedure. The sheath 200 may be introduced in a retrograde orientation, as shown, or alternatively, in some procedures, the sheath 200 and/or other devices herein may be introduced antegrade relative to the patient's blood flow, as appropriate for a given application.

Figure 1C:
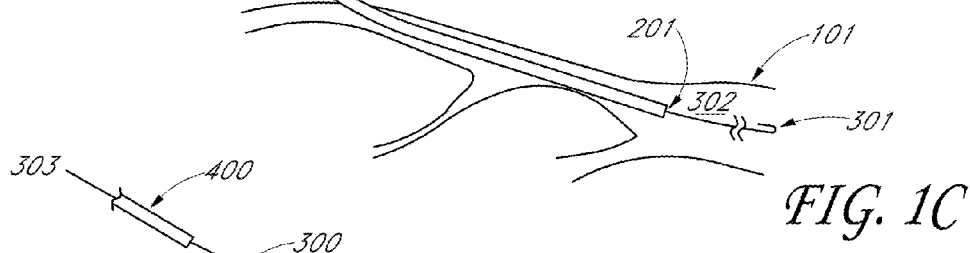
Figure 1D:
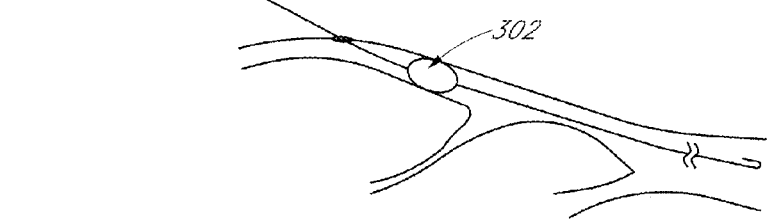

Upon completion of the catheter-based procedure, and before sheath withdrawal, an access wire balloon device or system 300 (for example, any of the embodiments described elsewhere herein or in the applications incorporated by reference herein) is inserted into the sheath 200 such that a tip 301 of the access wire device 300, for example, a floppy "J" tip, is positioned past the distal tip 201 of the sheath 200 inside the aorta 101, as shown in FIG. 1C. As described further elsewhere herein, the access wire device 300 may have a cross-section allowing the sheath 200 to be inserted/withdrawn/exchanged over the access wire shaft (and/or allow secondary devices to be advanced over the device 300). Thus, the sheath 200 may then be withdrawn (partially or completely) over the proximal end of the access wire device 300, for example, while maintaining the access wire device 300 in position. A balloon or other expandable member 302 on the access wire device 300 may be positioned and inflated at a desired occlusion site before, during, or after complete withdrawal of the sheath, for example, as shown in FIG. 1D.

Figure 1E:
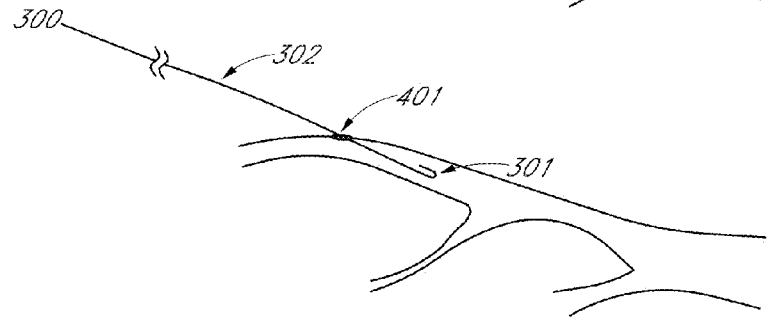

Upon sheath withdrawal (shown in FIG. 1D), the vascular access site may be closed, for example, with a suture/sealant combination 401, advanced about or otherwise in cooperation with the access wire device 300 at the site of arteriotomy, as shown in FIG. 1E. Exemplary closure devices and methods that may be delivered over or otherwise in conjunction with the access wire device 300 (or any of the embodiments herein) are disclosed in U.S. Pat. Nos. 7,316, 704, 7,331,979, 7,335,220 and 7,806,856, and U.S. Patent Application Publication Nos. 2007/0231366, 2008/0082122, 2009/0088793, 2009/0254110, 2010/0168789, 2010/0274280 and 2010/0280546. The entire disclosures of these references are expressly incorporated by reference herein.

The balloon 302 may be subsequently deflated, for example, as shown in FIG. 1E, and the access wire device 300 may be withdrawn through the closed arteriotomy. In these embodiments, the sealant 401 may be capable of closing the hole left by the access wire device 300 after withdrawal.

Figure 2A:
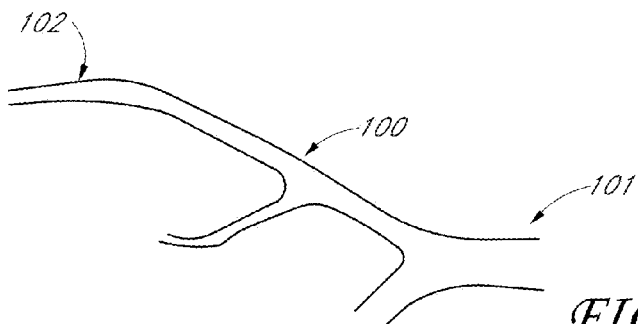
FIGS. 2A-2I show an exemplary method for stabilizing vascular injuries and managing blood flow during interventions.
Figure 2B:
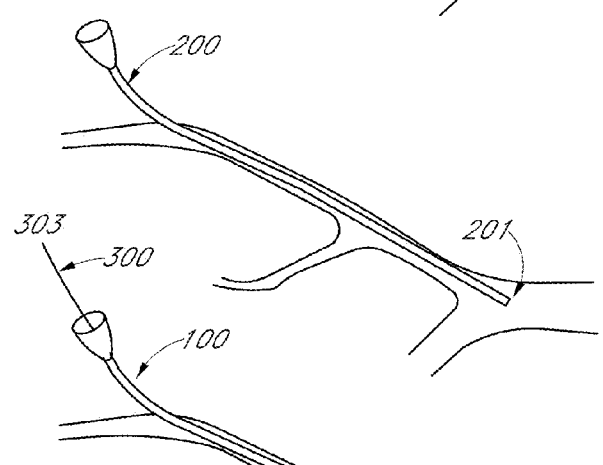
Figure 2C:
Figure 2D:
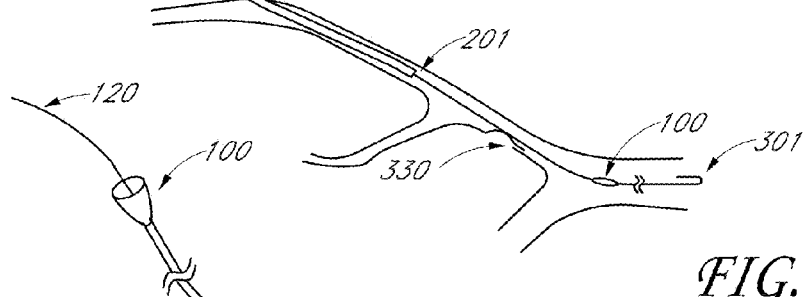
Figure 2E:
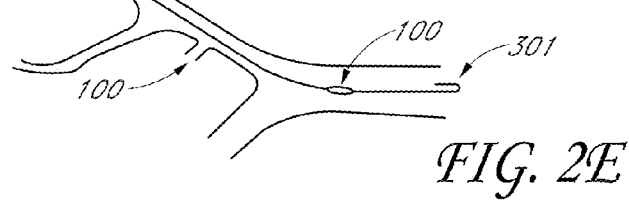

As shown in FIGS. 2A-2I, another method is provided for managing vascular complications and/or controlling bleeding during trans-femoral catheterization. The method may include inserting a vascular sheath 200 in the iliofemoral segment 100 for conducting a catheterization procedure, similar to the previous embodiment, as shown in FIGS. 2A and 2B. Upon completion of the procedure, and before sheath withdrawal, an access wire balloon device or system 300 (for example, any of the embodiments described elsewhere herein or in the applications incorporated by reference herein) is inserted into the procedure sheath such that a tip 301 of the access wire device 300 is positioned past the tip of the sheath 201 inside the aorta 101 (or other body lumen), as shown in FIG. 2C. The sheath 200 may then be withdrawn, for example, under angiographic guidance while maintaining the position of the access wire device 300.

Figure 2F:
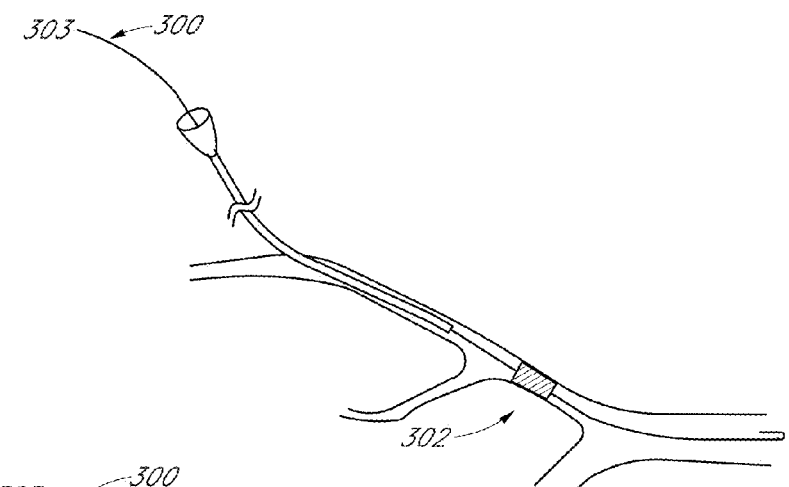

If sheath withdrawal uncovers a vascular injury, such as dissections 500 (shown in FIG. 2D) or perforations 600 (shown in FIG. 2E), expedient catheter management of the injury is possible by the access wire device 300, which is positioned in the true lumen of the vessel. As a first step, the balloon 302 may be positioned at the injury location 500, 600 and inflated, for example, as shown in FIG. 2F, in an effort to stabilize the vessel wall at the site of injury, and/or to bridge the complication for further treatment options. Subsequently, the access wire device 300 may provide a path for ipsilateral insertion of one or more additional devices 600, for example, suitable for managing such injuries, including regular and/or specialized catheters or other devices including balloons, stents, and/or other treatment elements.

Figure 2G:
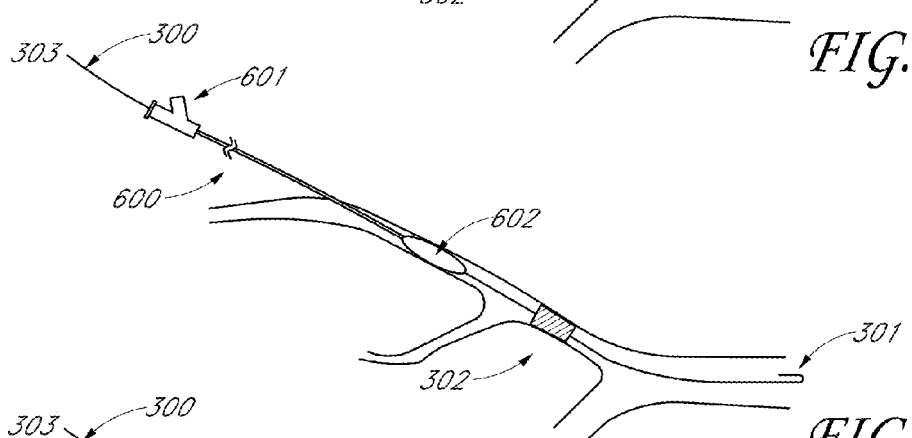
Figure 2H:
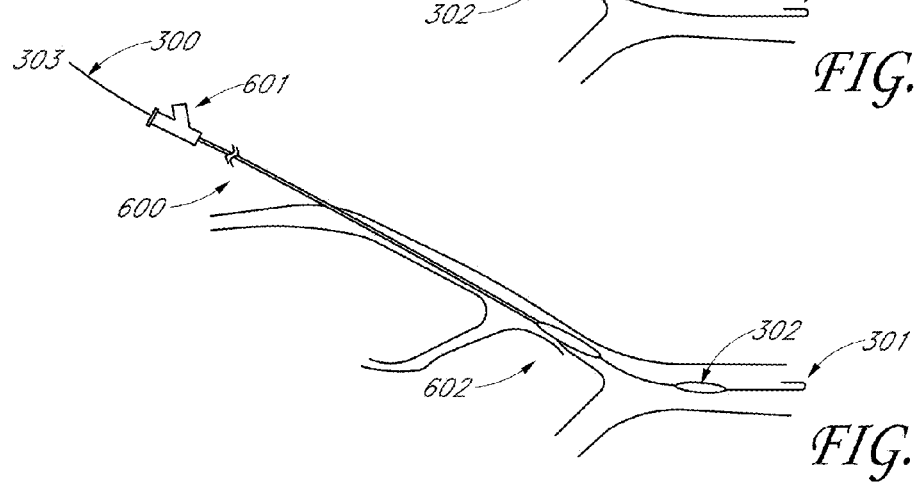
Figure 2I:
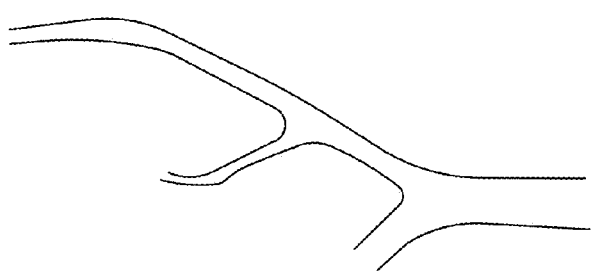

Under such scenarios, the device(s) 600 may be inserted into the target vessel over the access wire device 300 while the injury is stabilized and bleeding is minimized by the expanded balloon 302, for example, as shown in FIG. 2G-H. To facilitate positioning of a treatment device 602, the balloon 302 may be deflated and moved as desired within the vessel, for example, to an upstream location, as shown in FIG. 2H. Optionally, the tip 301 may be positioned past the iliofemoral segment 100 in the aorta 101 at any time during the procedure, for example, in order to prevent tip 301 related injury. In such procedures, the floppy tip segment 301 distal to the balloon 302 may be sufficiently long, for example, at least longer than the average length of the iliofemoral segment, such as at least about 15 cm or more preferably at least about 20 cm.

In various embodiments, the devices and systems herein may be inserted through the ipsilateral (interventionalist's) side of a patient or the contralateral side. Generally, in this application, "ipsilateral" refers to the side on which the main access was achieved for performing a given endovascular procedure. For example, the "ipsilateral femoral artery" or "ipsilateral iliofemoral artery" will generally be the artery in which a vascular access sheath is placed for advancing instruments to perform the intravascular procedure. "Contralateral" refers to the opposite side.

The tip 301 of the access wire device 300 may include special properties and/or features allowing for retrograde (against blood flow) insertion, maneuvering, and/or placement. For example, the device and/or system 300 may include a tip configuration, flexibility, radiopacity, rail support, core material, coating, and/or extension characteristics of an access wire (not shown). Alternatively or in addition, device length considerations and/or overall shaft stiffness may be modified accordingly.

Figure 3:
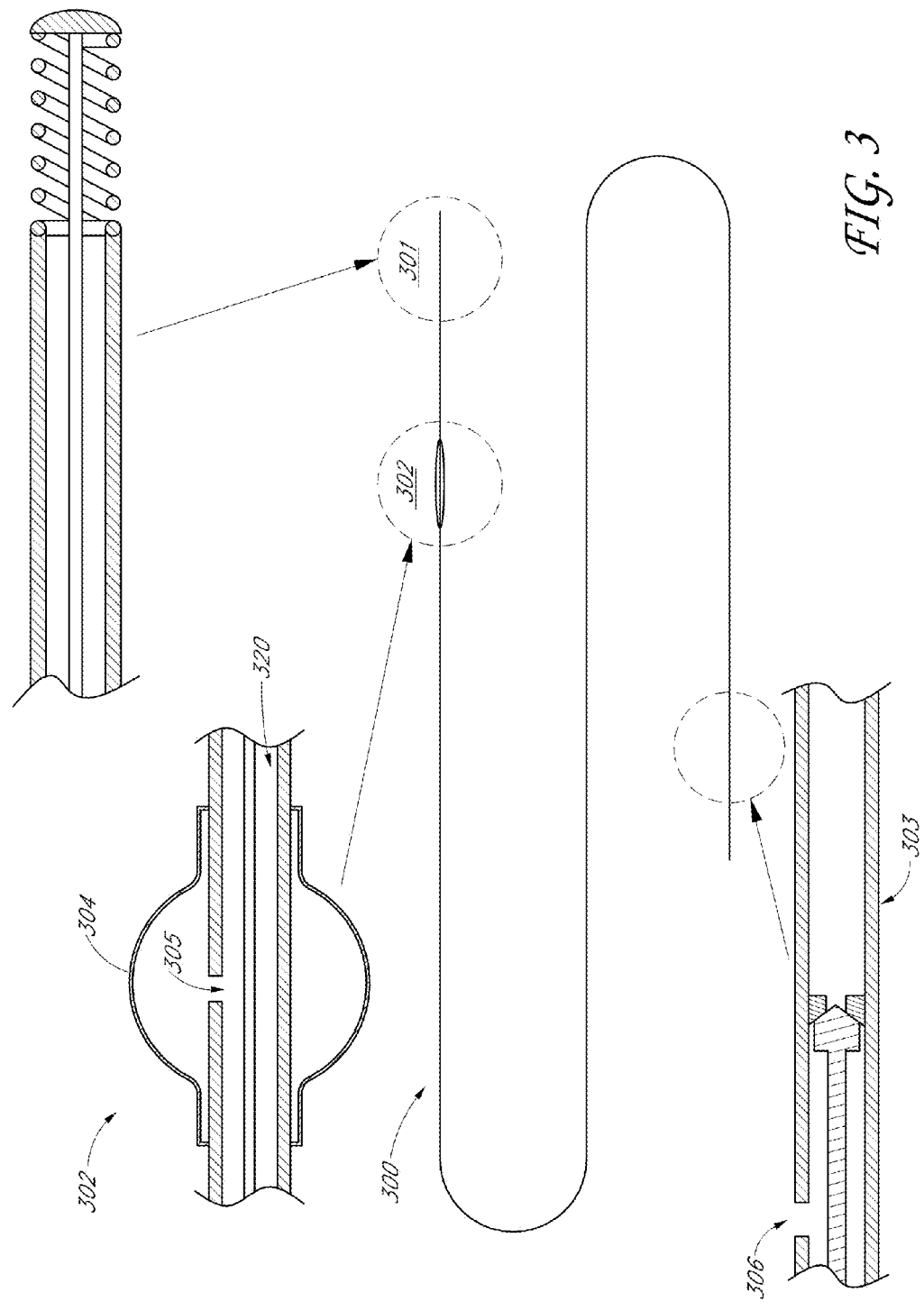
FIG. 3 includes a side view and details of an exemplary balloon device.

To perform the various procedures described herein, an access wire or balloon catheter device and/or system 300 may be provided for temporary endovascular flow occlusion during catheterization. Generally, as shown in FIG. 3, the device 300 may include a hollow access wire having a central lumen 320, an occlusion balloon or other expandable member 302 attached to or otherwise carried on a distal end of the access wire adjacent a distal tip of the access wire, and an inflation hub sealingly connectable to the extracorporeal or proximal end of the access wire.

The access wire device 300 may have dimensions and/or characteristics similar to conventional access wires. For example, the access wire device 300 may allow for introduction of other devices, such as catheters or other tubular devices carrying therapeutic and/or diagnostic elements (for example stents, covered stents, stent-grafts, balloons, etc.) In certain embodiments, the access wire device 300 (including the balloon 302 in a collapsed state) may be sized to be received in and/or to occlude an arterial or other body lumen, for example, sized between about 3 mm and about 15 mm in some embodiments and in other embodiments as large as about 30-40 mm. The access wire device 300 may also have a sufficient working length to allow introduction of other devices over the access wire shaft.

The entire length or the distal end of the access wire device may be made of compliant material that provides a flexible shape and/or accommodates the distal end conforming to the target lumen geometry. Alternatively, the proximal end 303 may be rigid, semi-rigid, or simply stiffer than the distal end to facilitate advancement of the access wire device 300 from the proximal end 303.

In some embodiments, the central lumen 320 of the access wire 300 may communicate with the external surface or environment of the device through a series of valves (or other flow regulators) for example, within or on the proximal end 303 of the access wire device 300.

In some embodiments, the deflated balloon 302 may have an overall low profile, substantially similar to the access wire shaft dimension, for example, such that at least the distal end has a substantially uniform diameter and/or the entire length of the access wire device 300 has a substantially uniform diameter.

In certain embodiments, the proximal end 303 of the access wire shaft may be attached to a detachable inflation unit for balloon 302 inflation/deflation. The inflation unit may be sealingly attached around or otherwise to the balloon shaft to provide inflation.

Some embodiments may include a fluid regulation system, for example, within the proximal end 303 of the access wire shaft, that maintains inflation/deflation state during operation, for example, when the inflation unit has been utilized to inflate or deflate the balloon 302 and then removed. The fluid regulation system may include a plurality of fluid regulators that are serially installed in order to maintain the balloon 302 in an inflation state, for example, in case of failure of an individual fluid regulator (for example, as a result of balloon catheter manipulation). In one embodiment, the fluid regulator system may include an internal fluid regulator and an external fluid regulator, which are operatively coupled such that opening the internal fluid regulator may cause the external fluid regulator to open as well. The fluid regulation system may also include one or more mechanisms designed to automatically lock at least one fluid regulator. In certain embodiments, the fluid regulator system may also include one or more protective features to prevent or minimize accidental manipulation, kinking etc., which may adversely affect inflation or deflation status. For example, one or more protective sleeves, caps, segments of enhanced stiffness, locking mechanisms, etc. (not shown) may be provided.

In one embodiment, the access wire shaft may be configured to accept parts that enable extension of the access wire shaft. For example, a shaft extension mechanism may be connected to the fluid regulator system in an effort to simplify overall design.

In certain embodiments, the access wire device 300 may be compatible with vascular closure devices, for example, utilizing sutures, clips, and other implants, etc. The access wire device 300 may also include one or more radiographic markers, for example, on the distal end adjacent to the balloon 302, to aid radiographic positioning.

FIG. 3 shows an exemplary embodiment of an access wire balloon device or system 300 that includes an access wire shaft or other outer tubular member including a proximal end 303, a distal end terminating in a substantially non traumatic distal tip 301, and a balloon or other expandable member 302 carried on the distal end. The balloon 302 may be formed from a soft membrane 304, for example, to provide a compliant balloon. The balloon 302 communicates with an internal access wire lumen 320 of the access wire shaft, for example, via one or more inflation ports 305 in a sidewall of the tubular member. Optionally, an internal wire may be provided within the access wire shaft, for example, within the lumen 320, to stiffen, straighten, or otherwise support the distal end or the entire length of the access wire shaft. The internal wire may be smaller than the lumen 320, as shown, for example, to accommodate fluid delivery through the lumen 320 around the internal wire. Optionally, the distal tip 301 may include a "J" tip and/or other features (not shown) beyond the balloon 302, similar to conventional access wires, if desired.

The proximal (extra-corporeal) end 303 of the access wire device 300 may be connected to an inflation device (not shown) for balloon inflation and deflation. In addition, the proximal end 303 may have an integrated flow regulator (valve) system designed to maintain balloon 302 inflation/deflation state, for example, when inflation device is disconnected, such as the embodiments described elsewhere herein and/or in the applications incorporated by reference herein.

Turning to FIGS. 4A and 4B, an exemplary embodiment of a fluid regulator (valve) system is shown that includes an internal piston 309 that may be directed to sealingly engage and disengage an internal valve 307 within the proximal end 303 of the access wire shaft, for example, when piston shaft 308 is moved axially relative to the access wire shaft. For example, as shown in FIG. 4A, the piston shaft 308 may be advanced distally until the piston 309 engages the valve 307 in a distal position. Thus, in the distal position, the lumen 320 of the access wire shaft may be substantially sealed, for example, after delivering sufficient fluid into the lumen 320 to inflate the balloon 302. Conversely, as shown in FIG. 4B, the piston shaft 308 may be retracted proximally until the piston 309 reaches a proximal position proximal to an outlet or side port 306 in a sidewall of the proximal end 303 of the tubular member. The internal lumen 320 may communicate with the external environment adjacent the proximal end 303 through the outlet 306 when the piston shaft 308 is retracted to the proximal position such that fluid may be delivered into or evacuated from the lumen 320, for example, to inflate or deflate the balloon 302 (not shown). Optionally, a low profile plunger (not shown) may be provided on the proximal end of the piston shaft 308 outside the proximal end of the access wire shaft to facilitate actuation of the valve system. Alternatively, a cap (not shown) similar to other embodiments herein may be provided on the proximal end of the access wire shaft that is coupled to the piston shaft 308. The cap may have a profile small enough to accommodate advancing supplementary devices (not shown) over the cap onto the access wire shaft. For example, the proximal end of the access wire shaft may be smaller than the adjacent length of the access wire shaft such that the cap provides a substantially uniform O.D. on the access wire device.

Turning to FIGS. 5A and 5B another embodiment of a fluid regulator (valve) system is shown that may be provided on the proximal end 303 of an access wire device, such as device 300 described above. In this embodiment, the internal piston 308 is driven by a spring 310, for example, a tension spring, which, in a substantially relaxed or relatively lower energy position (FIG. 4A) maintains a substantially sealed and/or closed fluid regulator (valve) system. As shown in FIG. 4B, when the piston 308 is moved distally relative to the access wire shaft, the internal valve 307 may be opened to allow communication between the internal lumen 320 and the external environment of the access wire device through outlet or side port 306. When the piston shaft is advanced distally to open the valve 307, the spring 310 may be subjected to increased tension such that, when the piston shaft is released, the piston shaft may resiliently retract proximally to engage the piston 308 with the valve 307 to automatically seal the lumen 320, for example, after inflating or deflating the balloon (not shown), similar to the previous embodiments.

FIGS. 6A and 6B show yet another embodiment of a fluid regulator (valve) system that may be provided on an access wire device, such as any of the embodiments herein, whereby an external cap 312 covers the outlet or side port 306 that communicates between the access wire internal lumen 320 and the external environment of the access wire device 300. The cap 312 may be moved relative to the outlet 306, for example, between a proximal position (shown in FIG. 6A) and a distal position (shown in FIG. 6B) to open and substantially seal the outlet 306, for example, to allow fluid to be delivered into and evacuated from the lumen 320, similar to the previous embodiments.

Figure 7A:
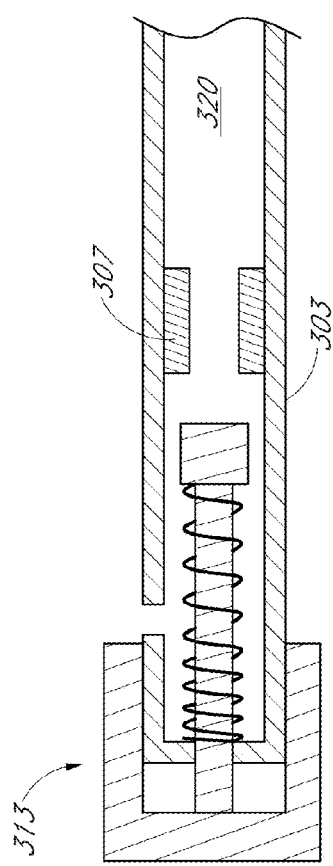
Figure 7B:
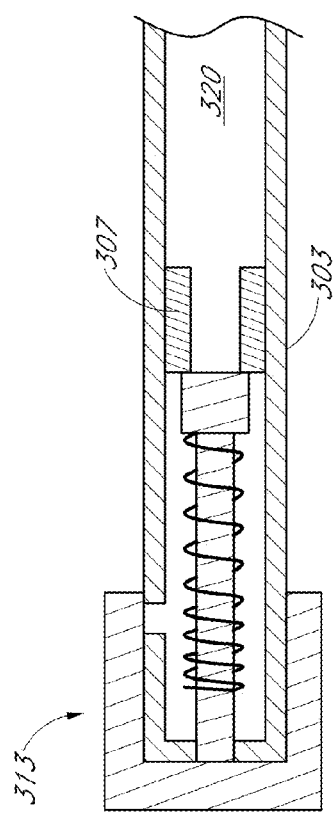
Figure 9A:
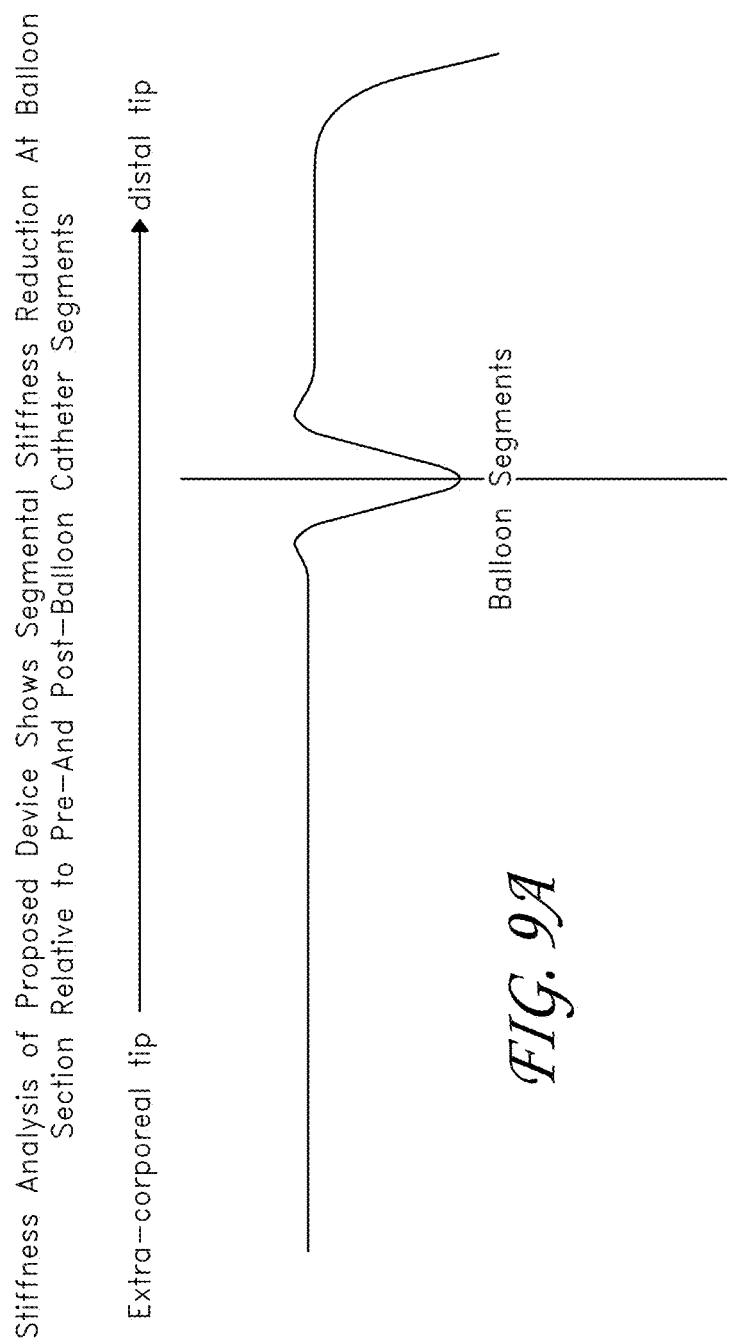
Figure 9D:
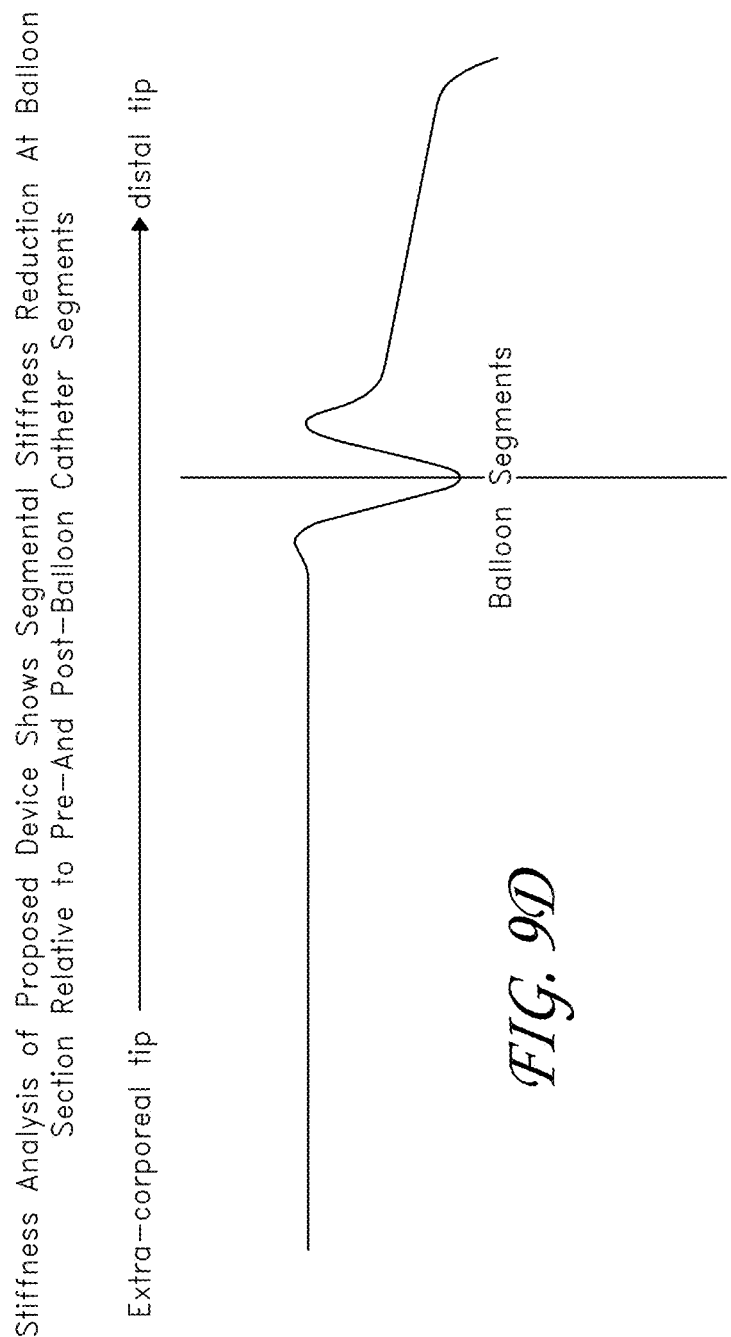
Figure 9E:
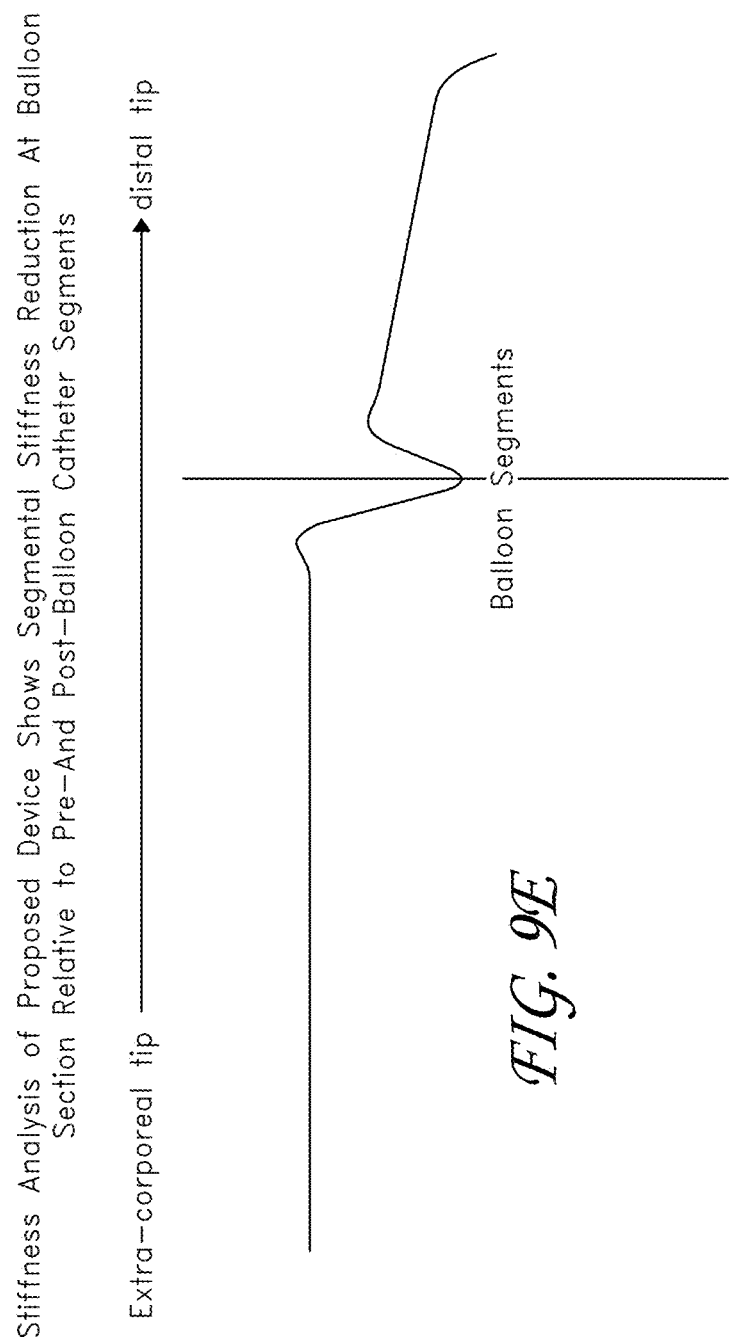

Turning to FIGS. 7A and 7B, still another embodiment of a fluid regulator (valve) system is shown that may be provided on a balloon access wire device. Unlike the previous embodiments, the system includes an internal valve element 307 and an external valve element 306, which are operatively (serially) connected such that a single actuation step may open both valves (as shown in FIG. 7A) or close them (as shown in FIG. 7B). Such a combination of valves may assure that flow within wire's internal lumen 320 is controlled to maintain a desired balloon inflation state.

In certain embodiments, devices and methods described herein may be compatible with existing devices and workflow, for example, such that the access wire device may be the last device to be removed from the target artery. Therapeutic device exchanges may be possible while vascular complications are stabilized endovascularly with a balloon. This may be especially significant, for example, if bleeding occurs at vascular segments that are inaccessible for manual compression (for example, the iliac artery, the proximal femoral artery, specific patient anatomy, etc.).

In certain clinical scenarios, there might be a need for the access wire device to be introduced before or during sheath advancement, i.e. through devices with true wire lumens, therefore the access wire device could have a uniform diameter over the entire length including the inflatable segment and the distal tip.

The devices and methods described herein may also ensure that access to the true lumen of the target vessel is maintained, when vascular complications are anticipated, but before they are encountered.

In some embodiments, the devices and methods described herein may facilitate an ipsilateral approach, for example, for better device control and improved blood loss management.

In certain clinical scenarios, it may be necessary to obtain angiographic guidance during insertion/withdrawal/maneuver of the access wire device. Therefore, the access wire device could incorporate mechanisms allowing for contrast injection at or close to the distal tip of the device. Such mechanisms may include channels, valves, and orifices for contrast injection. Alternatively, a custom sheath could be used in conjunction with the access wire device; said custom sheath is sufficiently dimensioned for housing the access wire device and allowing for simultaneous contrast flow. The custom sheath may be equipped with a contrast injection port and an extracorporeal valve that prevents contrast back-flow during injection.

In special clinical scenarios, it may also be useful to assess intravascular pressure, flow, temperature, general morphology, or other properties of the anatomy encountered, for example, to interrogate a special condition beyond angiography. In one embodiment, the access wire device or system may include elements providing physiological or image data during operation. These elements may include one or more pressure, flow, temperature sensors, and/or ultrasound, light, infrared, or other imaging elements. Additionally, one or more features may be provided for assessing intravascular dimensions, including balloon inflation dimension and/or pressure, for example, for estimating vessel sizes, and/or for targeting a specific inflation threshold.

The devices and systems herein may also have characteristics that allow it to be integrated into a robotic vascular surgery environment, such as the DaVinci system, the Zeus System, the Sensei system, etc.

In special scenarios, additional treatment to a body lumen or other target segment may be needed beyond balloon inflation. In one embodiment, the system may provide capabilities of local drug or agent or energy delivery through the access wire system, for example, more desirably through the balloon.

In special scenarios, it may also be useful to provide a source of therapeutic and/or diagnostic agents, for example, including one or more devices for injection of agents about the target treatment area. For example, the system may include a syringe, pump, or other source for intravascular injection of agents. Such access wire devices may include an extracorporeal injection port in the proximal end, an injection channel or other lumen, and/or a distal agent release port located in proximity to the balloon.

In certain clinical scenarios, the best therapy option is endovascular stent implantation. The access wire device could incorporate a stent delivery system that is readily available for treatment or in anticipation of vascular injuries.

The access wire device may integrate additional lumens for introduction of therapeutic/diagnostic agents/devices. Alternatively, the access wire system may be provided with a larger sheath that can be introduced over the wire, thereby forming a channel around the external surface of the wire.

In cases where prolonged flow occlusion is desired, it may be useful to provide simultaneous occlusion of target region, and perfusion of distal regions. Therefore, the access wire device or system may include tissue perfusion across the balloon occlusion area. Such features may include perfusion channels in the shaft or balloon, for example, with appropriate ports, valves, and/or flow drivers.

In special clinical scenarios, it may be useful to isolate a specified segment of a body lumen for diagnostic or treatment purposes. In one embodiment, the access wire system can be combined with a standard balloon catheter to create a double-balloon catheter system that is capable of isolating a targeted vessel or other bodily passages.

In certain embodiments, the balloon may provide an anchoring mechanism for the access wire device, for example, such that over-the-wire device insertion is facilitated.

In certain embodiments, the occlusion balloon may be conforming to the lumen shape, and may grow axially/longitudinally during inflation. The balloon could exhibit varying wall thicknesses to provide preferential inflation shape. For example, thinner sections inflate first followed by thicker sections as the thin walled portions contact the vessel wall. The balloon could be corrugated by thicker wall sections or Kevlar inflation restrictions to mitigate pressure on the vessel wall.

In some scenarios, balloon occlusion/inflation is required over long vascular segments. One embodiment could incorporate a device shaft with multiple balloon units that collectively cover a longer vascular segment. The balloon units could be collectively or individually connected to the same/multiple inflation system(s).

In certain clinical scenarios, balloon dilatation might be required. The access wire balloon device could incorporate a balloon that fulfills occlusion and dilatation function.

In one embodiment, the access wire device could be a closed system with balloon inflation agent stored inside a sealed tubing system. Collapse (or expansion) of the internal lumen of the tubing system would move the fluid into (or away) from the balloon thereby causing balloon inflation (or deflation). This embodiment foresees a tubing system that is not in communication with the external surface and has a pre-installed balloon inflation agent.

In special clinical scenarios, it may be desirable to have a system for facilitating device insertion through tortuous vascular segments. For example, it might be desirable to have an access wire device or system that includes a flexible tip designed for retrograde insertion and a stiffer shaft proximal to the tip designed for facilitating over-the-wire device insertion through tortuous segments.

In certain clinical scenarios, vessel tortuosity may require straightening in order to ease device (sheath) insertion/retraction. The access wire device could have a stiff shaft capable of non-traumatic straightening originally tortuous vessel. The stiffness could vary along the length. The distal section should be flexible and atraumatic.

In certain clinical scenarios, vessel tortuosity may require intravascular shape change of the distal tip. The proposed system may integrate steerability mechanisms that allow for temporary shape change of individual segments of the device.

In certain clinical scenarios, the target treatment segment could be rigid-tortuous, and does not respond to straightening attempts, therefore it would desirable for the balloon to adapt to vessel tortuosity. In one embodiment, the inflatable segment could integrate a flexible segment or joint that allows for the inflatable segment to bend and provide flexibility to otherwise a stiff segment, as shown in FIG. 8. The joint must not impact the balloon inflation functionality.

In certain clinical scenarios, insertion or advancement of the access wire device requires a minimum of catheter shaft backbone support (stiffness). This access wire characteristic is required for segments of the access wire device such as the device shaft and the proximal part of the distal tip. FIGS. 9A-9E provide scenarios of the stiffness characteristics of the individual segments of the access wire device.

In some embodiments, the removable inflation handle may integrate a torque system that provides torqueing of the access wire device during operation if desired.

Figure 10:
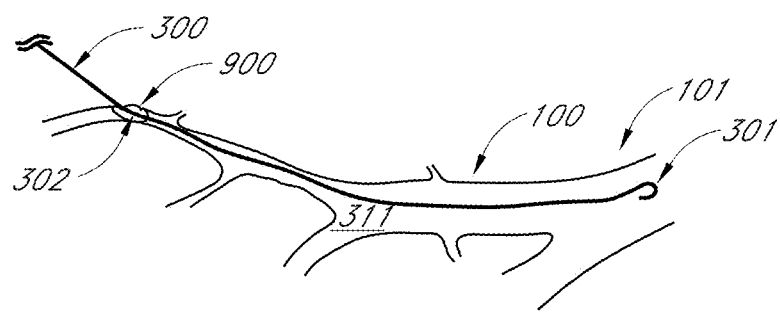
FIG. 10 illustrates the dimensions of one embodiment of the device disclosed herein, in position across an iliofemoral segment.

In certain clinical scenarios, it is necessary to provide occlusion 302 at the level of the femoral arteriotomy 900, while maintaining position of the distal tip in the aorta 101. It is therefore desirable for the distal end 311 to be of sufficient length to extend through the iliofemoral 100 segment and be safely positioned (during femoral occlusion) in the aorta, as shown in FIG. 10. In a preferred embodiment, the outer diameter of the access wire device is between 0.014 and 0.038 inches. In a preferred embodiment, the length of the distal tip is between 20 and fifty centimeters. Optionally, the distal tip 301 may include a "J" tip and/or other features (not shown) beyond the balloon 302, similar to conventional access wires, if desired.

Figure 11:
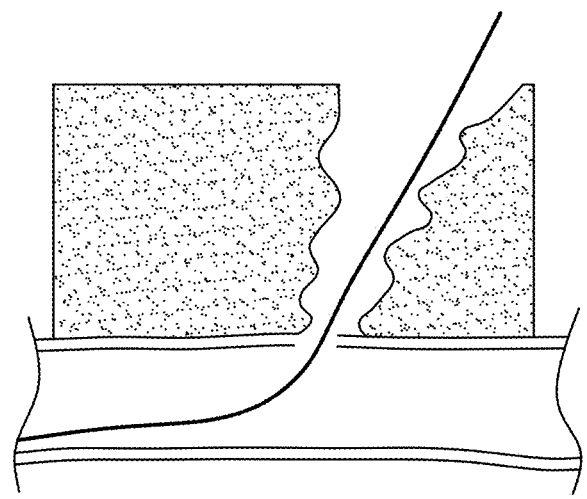
FIG. 11 illustrates one embodiment of the access wire device having a flexible distal end, extending across a nonlinear path at the vascular access site.

In certain embodiments, as shown in FIG. 11, the distal end of the access wire device is capable of bending at sites of procedural bends such as the site of percutaneous catheter insertion.

Figure 12:
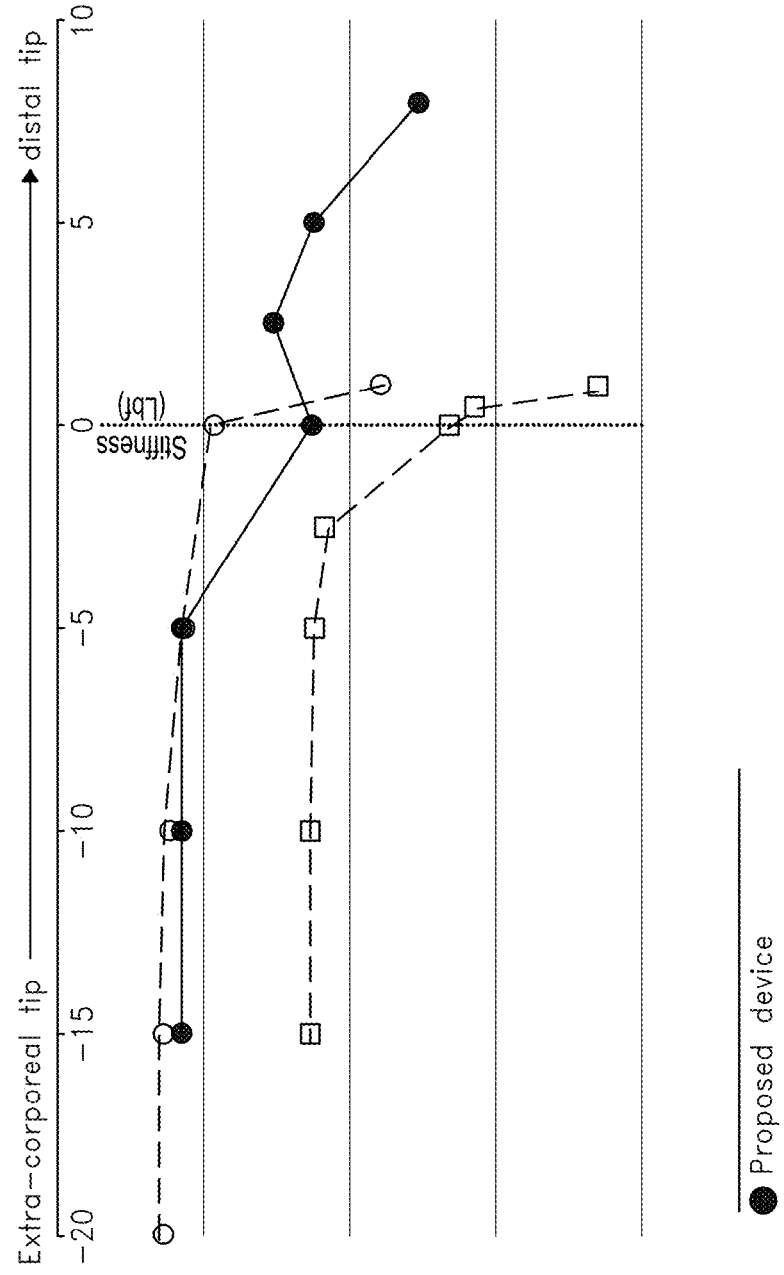
FIG. 12 illustrates experimental results comparing the stiffness characteristics of the access wire device with existing products.

Several catheter characteristics such as pushability, trackability, and adaptability to vessel tortuosities are directly related to stiffness patterns of the catheter along its shaft. To determine the appropriate stiffness patterns for the access wire device described herein, the following experiment was performed. The device disclosed herein was compared to the Guardwire balloon system (Medtronic PercuSurge, 0.014") and the Guideright access wire (St. Jude, 0.038"). Each device was inserted into a catheter fixture and the region of interest was aligned with the fixture. After the Instron was calibrated with regard to push force, deflection, and position, the Instron was advanced to cause a 5 mm deflection at the region of interest. Deflection force (LbF, N) and position of deflection (distance from inflatable segment) were recorded. The procedure was then repeated for each additional region of interest. The experimental results are illustrated in FIG. 12.

Two catheters, the access wire device disclosed herein and Guardwire, showed comparable stiffness profiles at the distal tip. The access wire device, however, showed a different stiffness profile marked by the segmental decrease in stiffness at the balloon segment (position 0) relative to the proximal catheter shaft and the distal tip. This functionality lends a special flexibility feature to the balloon and allows for balloon occlusion at sites of significant tortuosity (where complications are expected), and/or at sites of procedure induced bends (such as transitions from tissue tract into arteriotomy).

Figure 13:
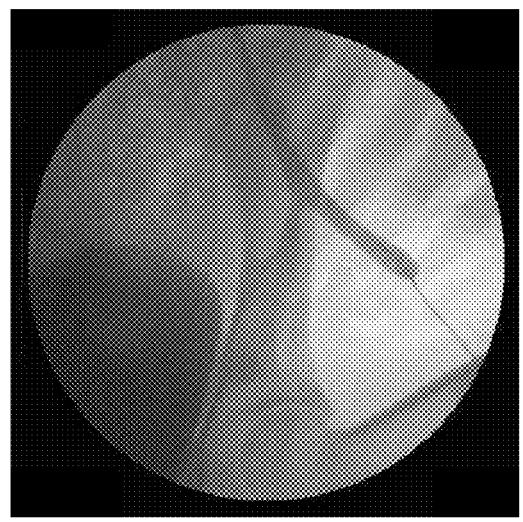
FIG. 13 shows an angiogram of the access wire device's ability to occlude blood flow.
Figure 14:
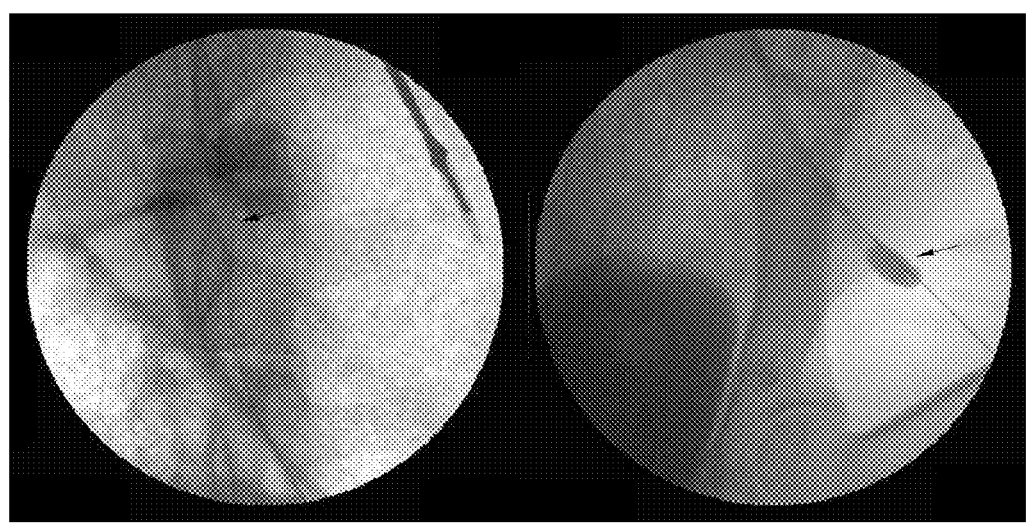
FIG. 14 shows angiographic images of the access wire device extending from the iliofemoral segment to the aorta.

The utility of the access wire device was successfully tested in the sheep and showed that the intended design of decreased flexibility at balloon segment allowed for balloon occlusion at sites of significant tortuosity (where complications are expected), and/or at sites of procedure induced bends (such as transitions from tissue tract into arteriotomy). FIG. 13 shows an angiogram of the sheep femoral artery at the site of 18Fr arteriotomy showing the access wire device's ability to occlude blood (contrast) flow at the site of percutaneous catheter insertion (arteriotomy). FIG. 14 is an angiographic image showing a clinical scenario where an occlusion at the femoral arteriotomy is required (right panel). In this scenario, it would be desirable for the J-tip of the distal tip to be of sufficient length to extend through the iliofemoral segment, and be safely positioned (during femoral occlusion) in the aorta (left panel).

Referring now to FIGS. 15A-15K, in another embodiment, an access wire balloon catheter may be advanced through a contralateral access catheter to treat a vascular injury in an ipsilateral iliofemoral artery. For the purposes of this disclosure, the terms "ipsilateral" and "main" may be used interchangeably to refer to the artery, access site or side of the body in which the main vascular access sheath is placed to perform an intravascular procedure. The terms "contralateral" or "secondary" or "accessory" may be used interchangeably to refer to the access side, artery or side of the body opposite the ipsilateral or main access site. In some embodiments, to be described below, the "secondary access site" is used to introduce the access wire balloon device, which is then advanced over to the main/ipsilateral side. The secondary (or contralateral) access site may be a contralateral femoral artery, iliofemoral artery or other access vessels such as but not limited to a contralateral radial or subclavian arteries or other peripheral or aortic access sites. The phrase "iliofemoral artery" may include the femoral artery, the common iliac artery or an iliofemoral segment including part of the femoral artery and part of the common iliac artery. The embodiments described above generally involve accessing and treating the main (ipsilateral) iliofemoral artery via an access site in the ipsilateral femoral artery. In the embodiment described below in reference to FIGS. 15A-15K, however, a different approach with access through a secondary, contralateral access site is used.

Figure 15B:
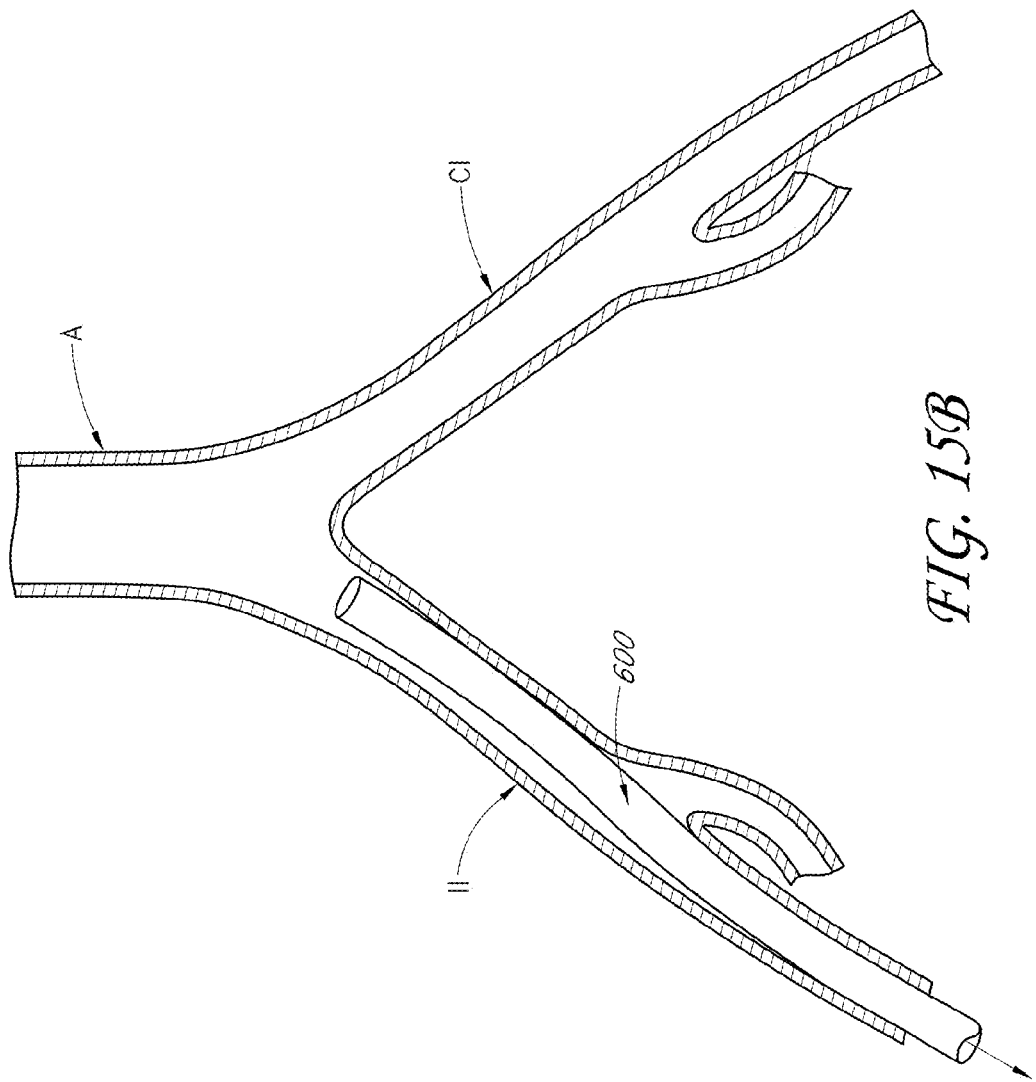

Referring to FIGS. 15A and 15B, a vascular access sheath 600 is shown in place within an ipsilateral iliofemoral artery II ("main access site"). In FIG. 15A, access sheath 600 is shown with its tip in the aorta A, and in FIG. 15B, access sheath 600 is shown slightly retracted (solid-tipped arrow) so that the tip resides in the common iliac artery. In large bore intravascular procedures, vascular access sheaths 600 typically have an outer diameter of 18F-20F, which is much larger than small bore access catheters and which is a diameter that can be damaging to an iliofemoral artery.

Figure 15C:
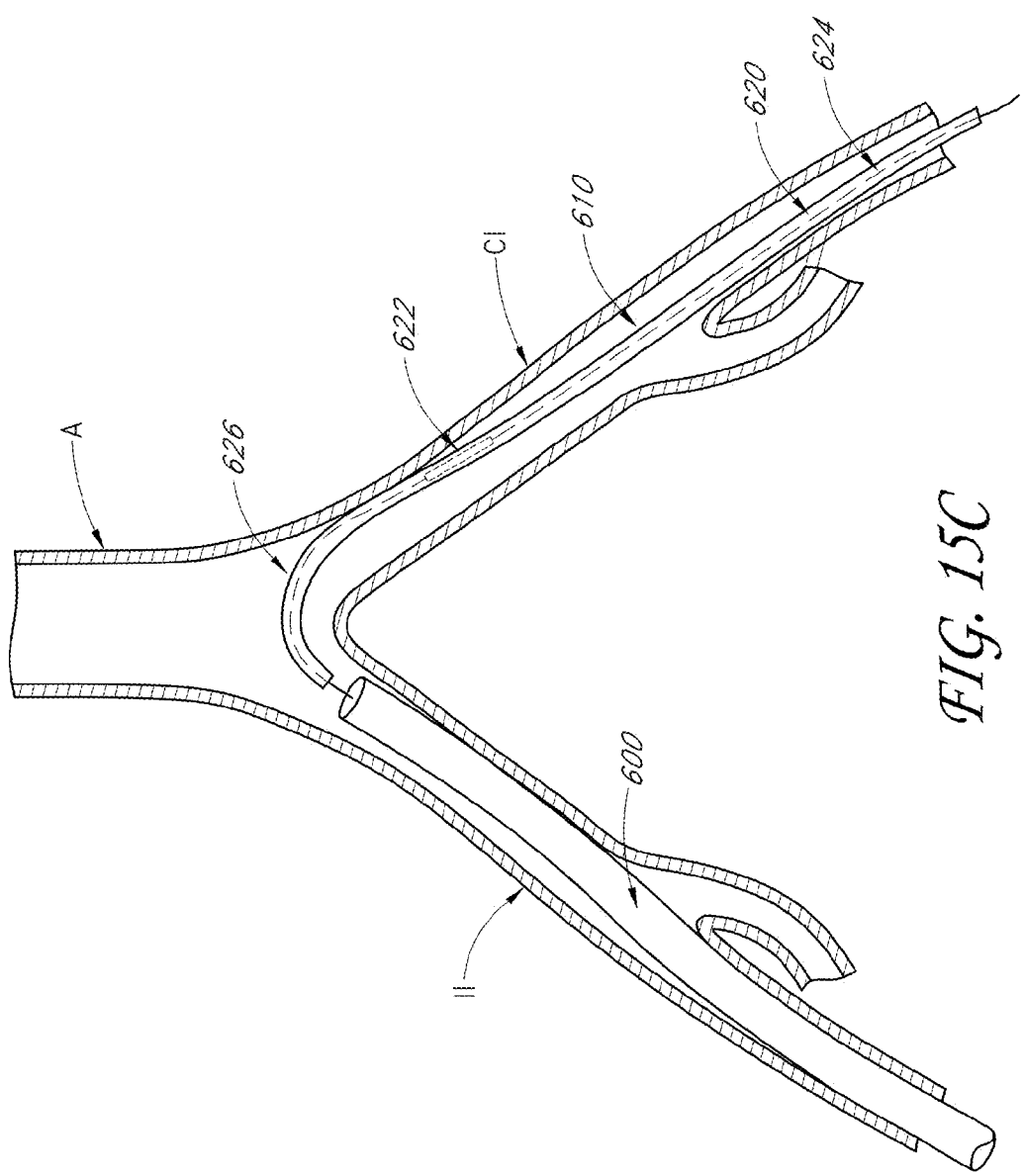

Now referring to FIG. 15C, in most intravascular procedures, a contralateral access catheter (not shown) is placed through the contralateral iliofemoral artery (or "secondary access site") for injection of contrast dye during the procedure (for external visualization of the procedure using fluoroscopy or other radiographic techniques). In some embodiments, this previously placed catheter may be used to advance an access wire balloon 620 into the ipsilateral iliofemoral artery II (or "main access site"). In other embodiments, the previously placed access catheter may be removed and another, pre-shaped, contralateral access catheter 610 may be introduced into the contralateral iliofemoral artery CI. Contralateral access catheter 610 has a curved distal portion to help navigate the aortic bifurcation, which may facilitate advancing access wire balloon 620 into the ipsilateral iliofemoral artery II. In some embodiments, contralateral access catheter 610 may be preshaped with a curve in its distal end to facilitate navigating around the aortic bifurcation.

As described above, access wire balloon 620 typically includes a central lumen for inflation (not visible), an inflatable balloon 622 (or other expandable member in alternative embodiments) in fluid communication with the lumen, a proximal portion 624 that starts out relatively stiff at the extreme proximal end and gets increasingly more flexible toward balloon 622, a flexible distal portion 626 that is most flexible at the extreme distal end, and a locking valve on proximal portion 624 that allows for inflation, deflation and maintenance of inflation of balloon 622. In generally, access wire balloon device 620 has a length and stiffness profile that allows it to be advanced through a relatively small access catheter 610, through the aortic bifurcation, and into vascular access sheath 600 in the ipsilateral iliofemoral artery II without requiring additional guidewires or catheter exchanges.

Figure 15D:
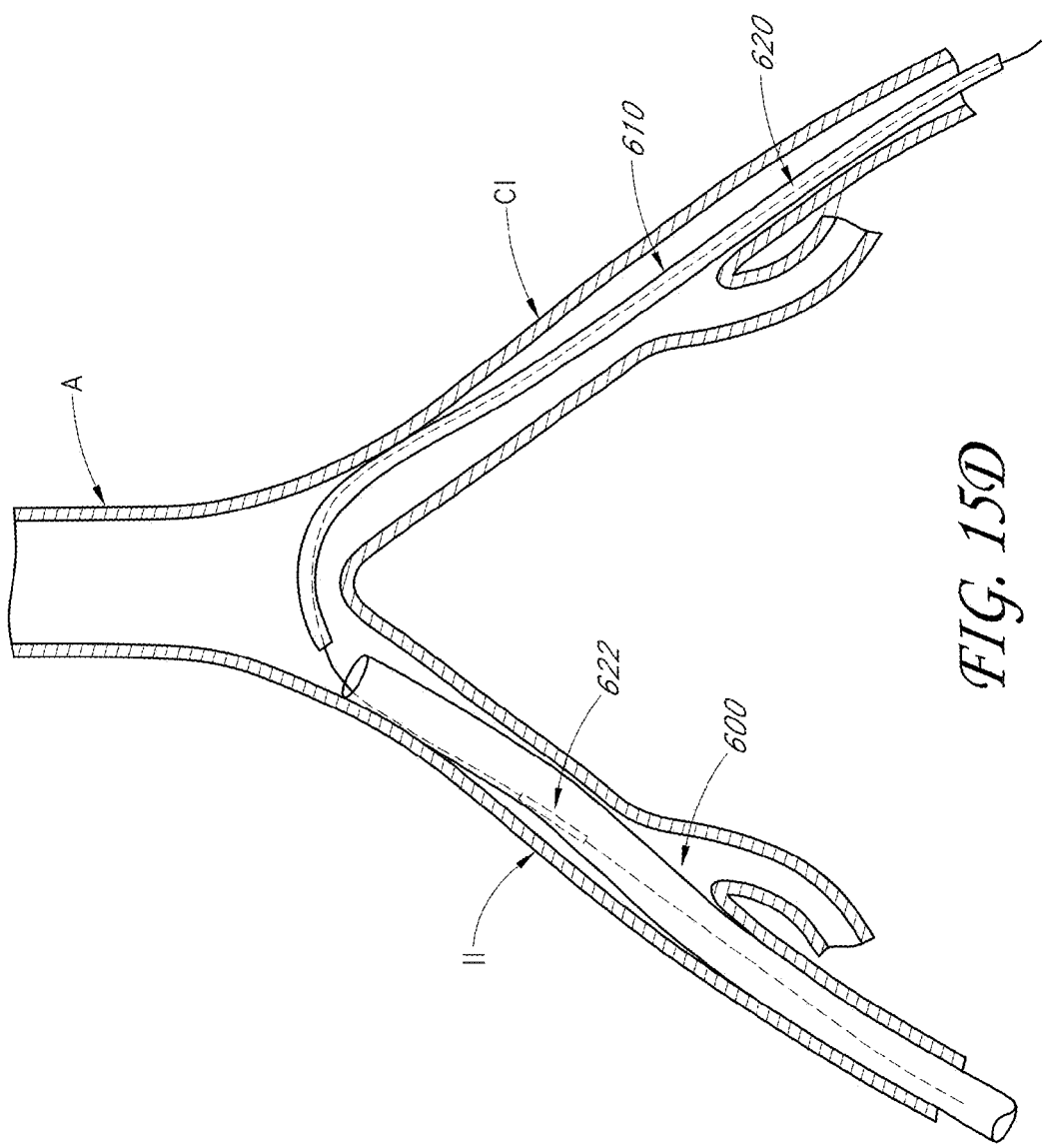
Figure 15E:
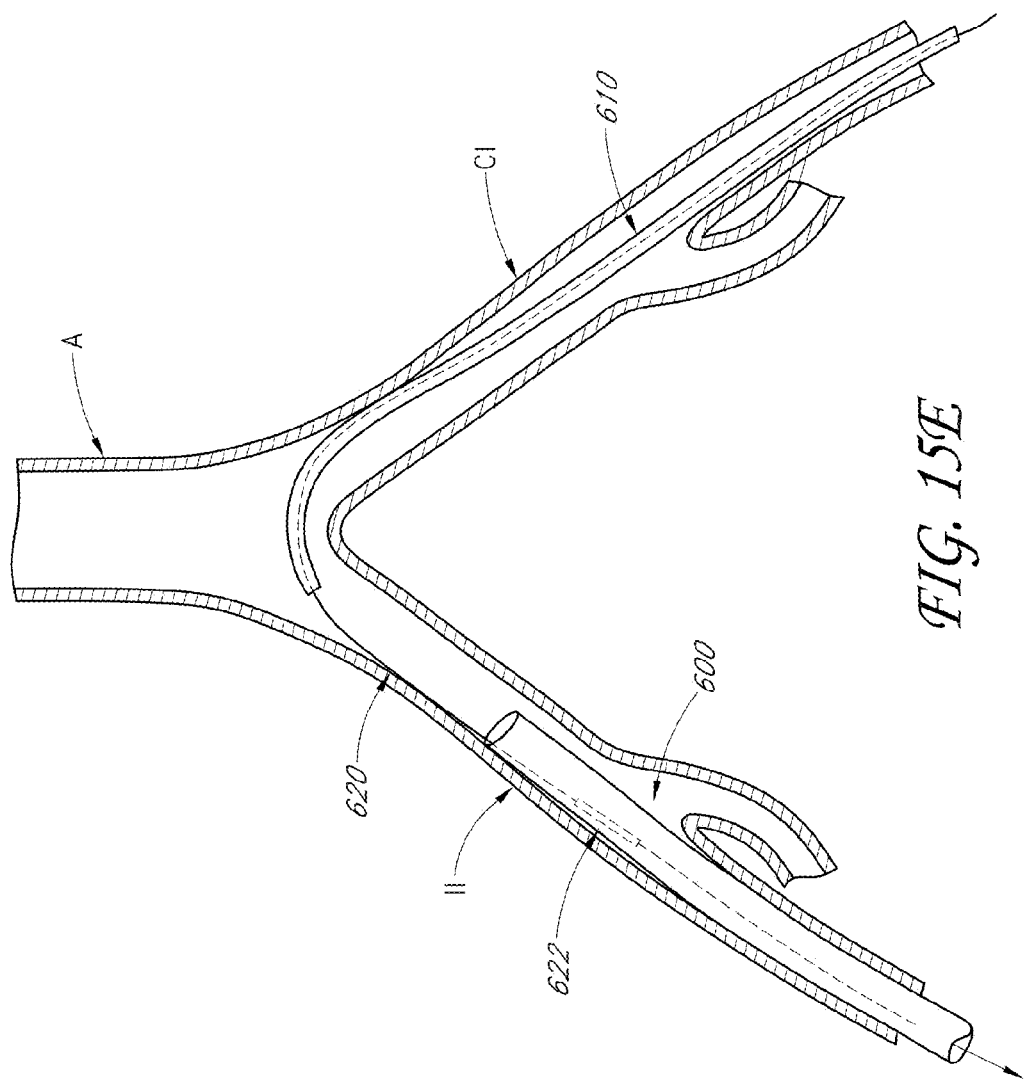
Figure 15F:
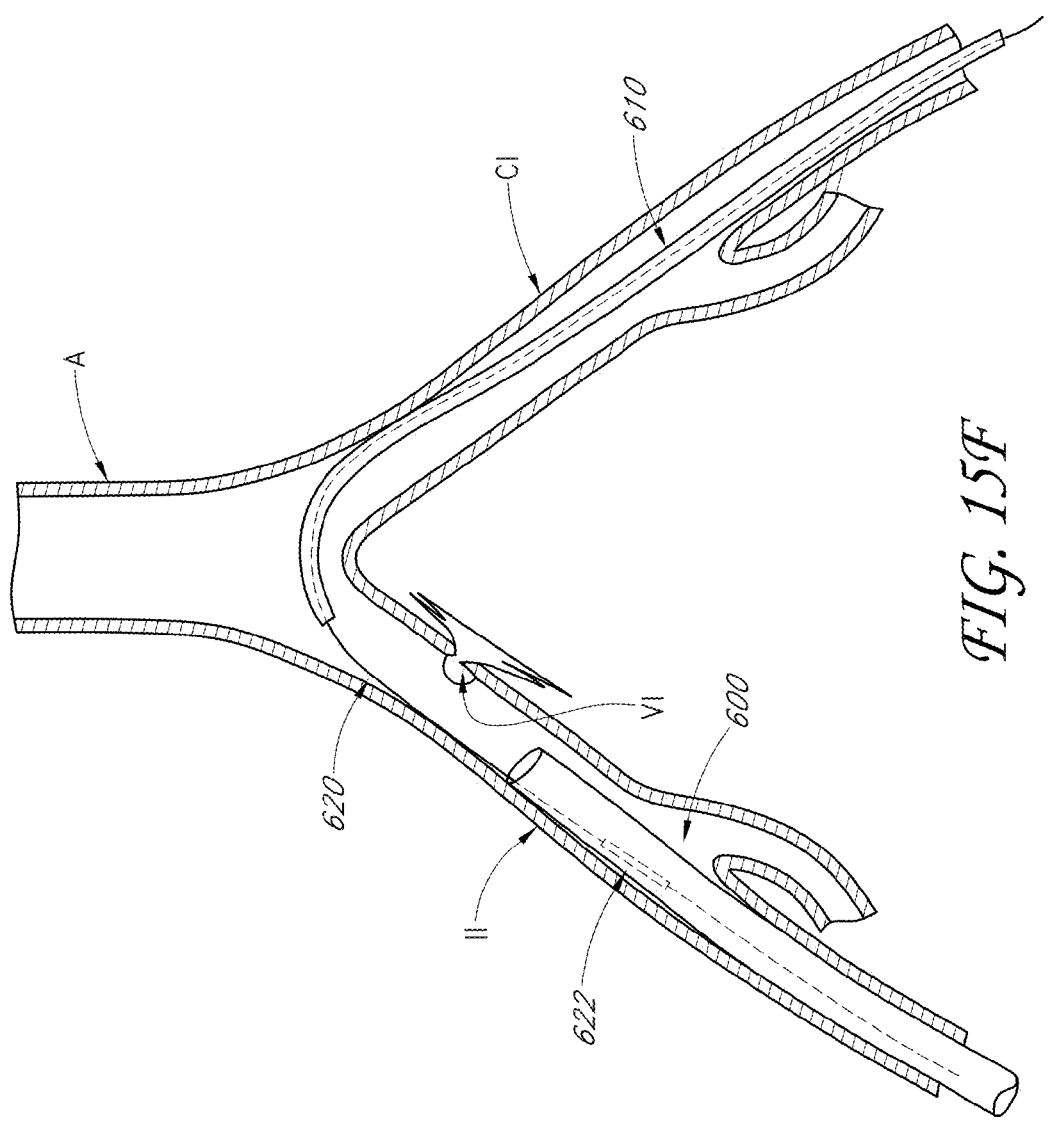

With reference now to FIGS. 15D-15F, once balloon 622 is advanced into vascular sheath 600 (FIG. 15D), sheath 600 may be withdrawn at least partway out of the ipsilateral iliofemoral artery II (FIG. 15E, solid-tipped arrow), which may reveal a vascular injury VI with hemorrhaging. The vascular injury VI and hemorrhage may be detected, for example, by injecting contrast and viewing the ipsilateral iliofemoral artery II via fluoroscopy during and/or after withdrawal of vascular sheath 600. In some embodiments, for example, access wire balloon 620 may be used for one or more contrast injections. In another method (not shown in 15F), the inflatable balloon 622 may be inflated inside vascular sheath 600 and then used as anchoring mechanism for the access wire 620 and to provide backbone support during the introduction of secondary devices (not shown) over access wire shaft 620.

Figure 15H:
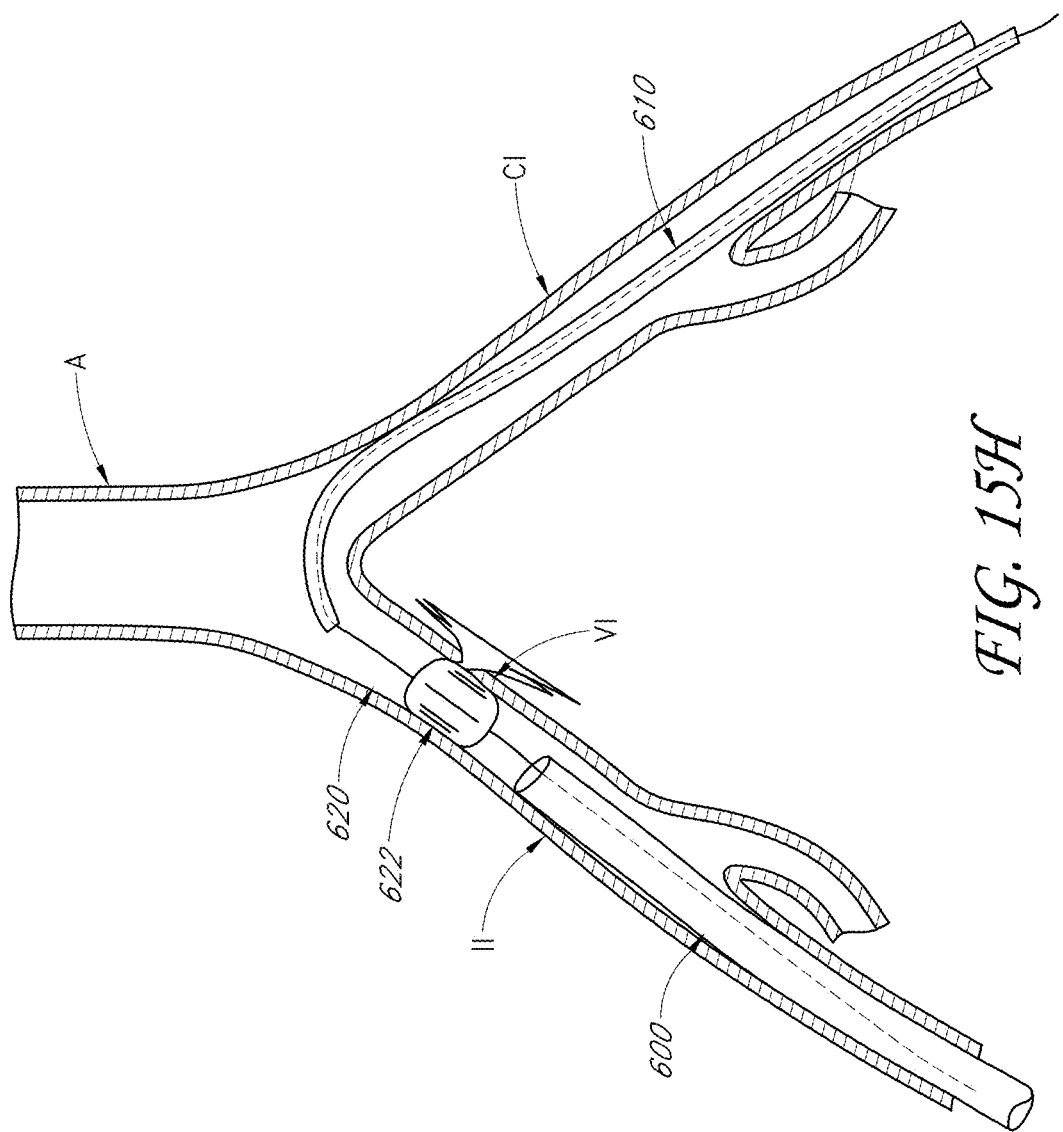

As shown in FIGS. 15G and 15H, balloon 622 may next be repositioned at the location of vascular injury VI (FIG. 15G) and inflated (FIG. 15H) to stop bleeding at the injury site. In this way, the injury can be stabilized while treatment is contemplated and started. Once balloon 622 is inflated, an inflation device (not shown) may be removed from proximal portion 624 of access wire balloon 620, thus leaving a hubless proximal end and also maintaining balloon 622 in an inflated configuration, due to the locking valve of device 620. At this point, one or more intravascular treatment devices, such as stent delivery devices or the like, may be advanced over proximal end 624 of access wire balloon 620 to perform a repair on the ipsilateral iliofemoral artery II. In an alternative embodiment, balloon 620 may be inflated near the vascular injury VI (rather than over it) to stop or reduce bleeding.

Figure 15I:
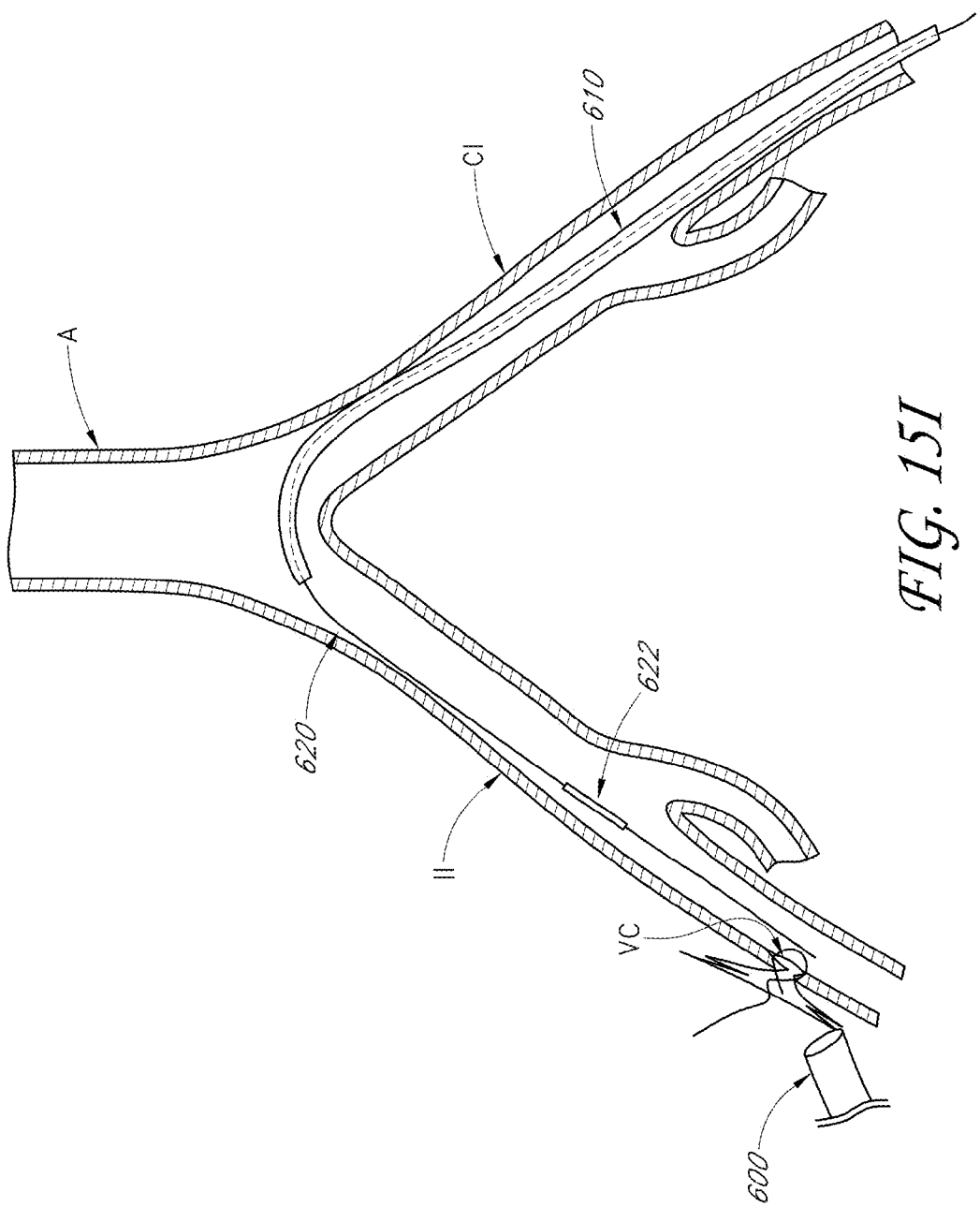
Figure 15J:
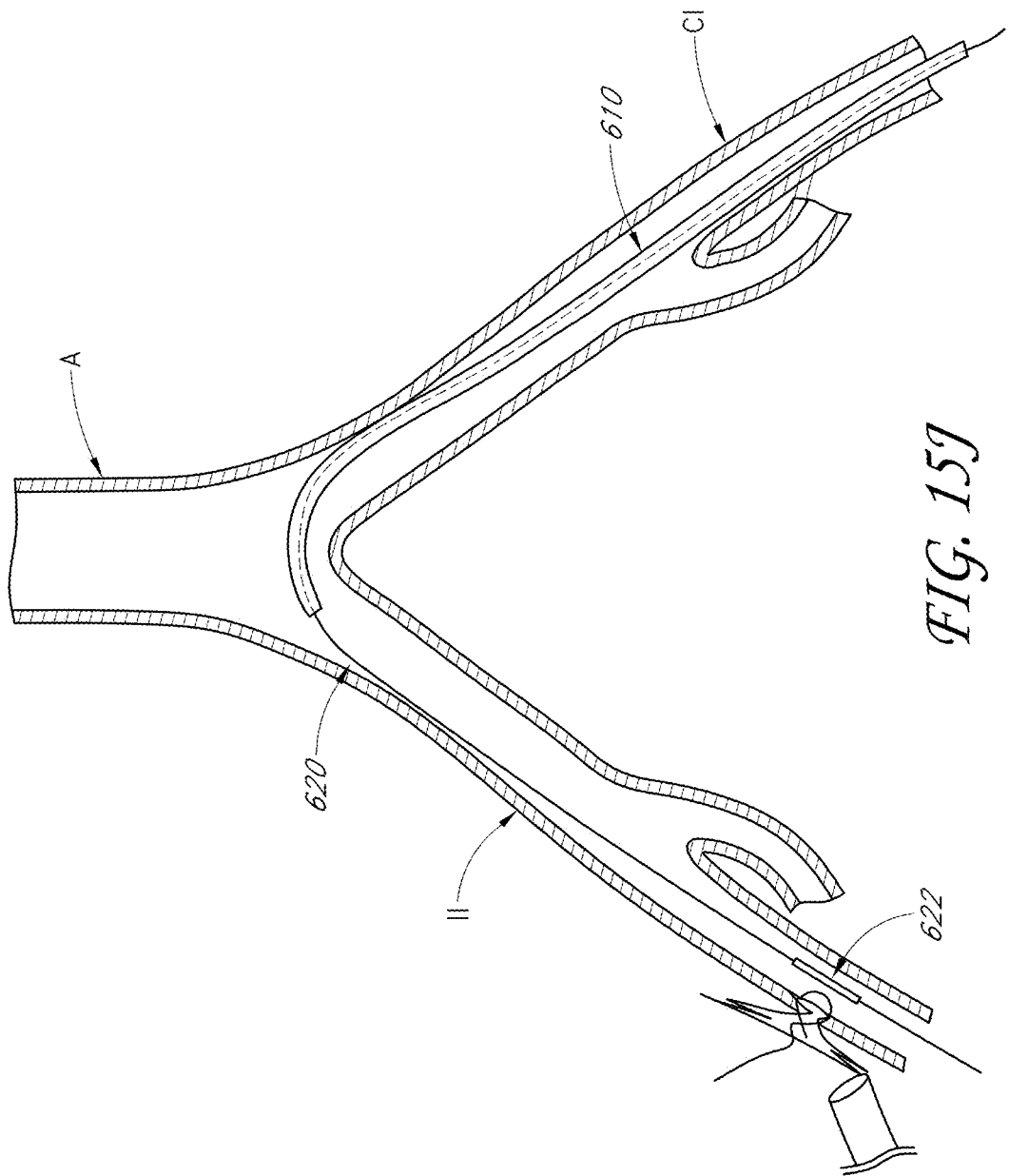
Figure 15K:
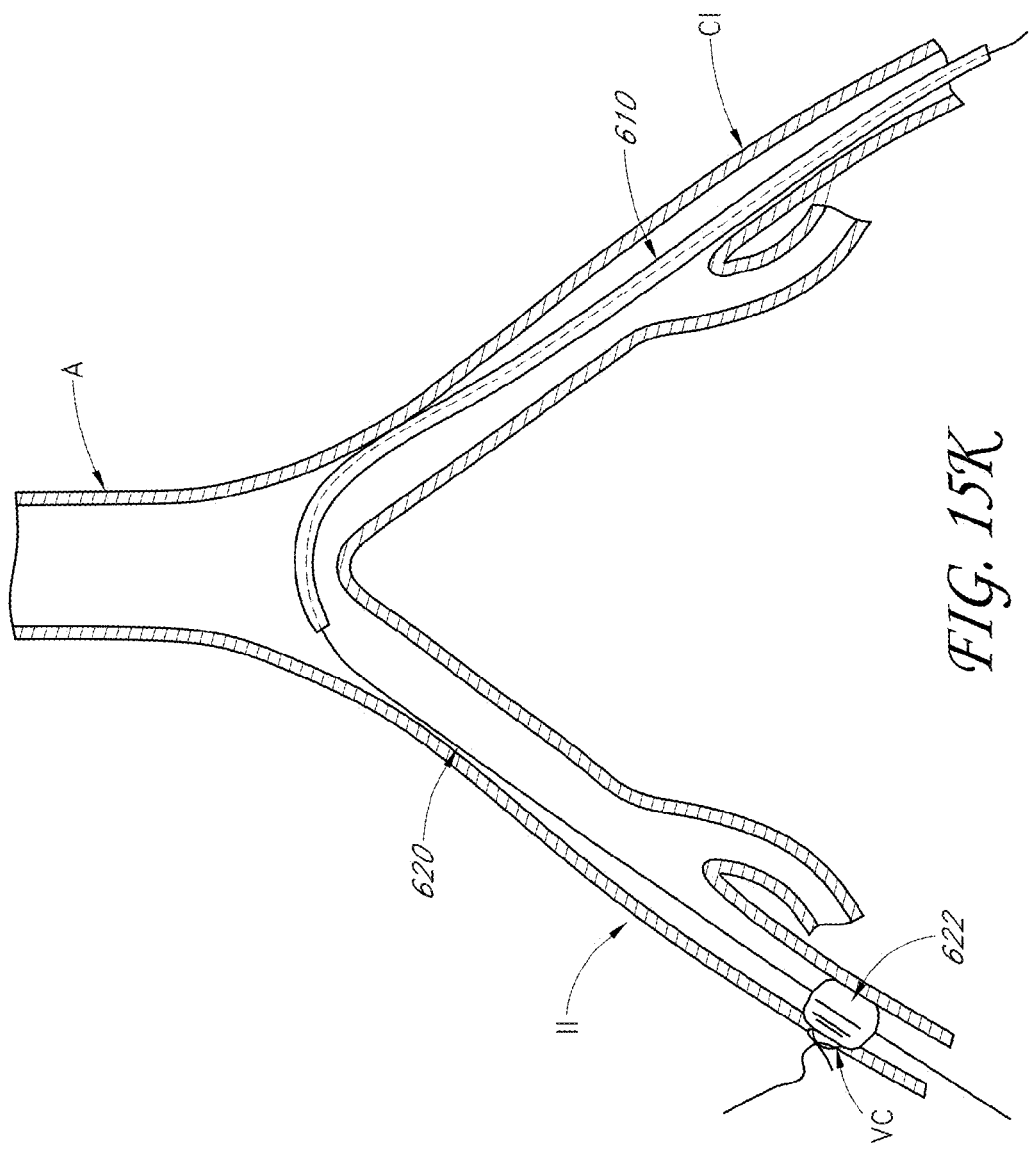

Referring now to FIGS. 15I-15J, in some embodiments, after vascular sheath 600 is removed from the ipsilateral iliofemoral artery II, a vascular complication (i.e., bleeding) may be detected at the arteriotomy site (FIG. 15I). The arteriotomy generally refers to the opening purposely made in the artery for advancing vascular sheath 600 into the artery. Closing the arteriotomy at the end of the procedure can sometimes be a challenge. Once bleeding is detected, access wire balloon 620 may be advanced to position balloon 622 at the arteriotomy site (FIG. 15J) and balloon 622 may be inflated (FIG. 15K) to control bleeding. Just as with the earlier vascular injury, one or more treatment devices may be advanced over access wire balloon 620 to help close the arteriotomy.

Elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives thereof.

The invention claimed is:

1. A method of treating a vascular injury occurring during or after an intravascular procedure, the method comprising:
    advancing an access wire having an inflatable balloon integral to the wire through a previously placed access catheter in a contralateral femoral artery to position the inflatable balloon integral to the access wire in a vascular access sheath located in an ipsilateral femoral artery, without using any additional guidewires to advance the access wire;
    withdrawing the vascular access sheath at least partway out of the ipsilateral femoral artery to expose the vascular injury;
    inflating the balloon to occlude the ipsilateral femoral artery or an ipsilateral iliofemoral artery at or near the vascular injury;
    removing an inflation device from a proximal portion of the access wire, wherein a proximal end of the access wire is hubless, and wherein the balloon remains inflated after inflation device removal;
    advancing at least one treatment device over the hubless proximal end of the access wire; and
    treating the vascular injury using the at least one treatment device.

2. The method as in claim 1, wherein the access catheter is placed in the contralateral femoral artery before or during the intravascular procedure to provide contrast dye or other instruments during the procedure.

3. The method as in claim 1, wherein the access catheter comprises a curved distal portion for navigating around the aortic bifurcation, and wherein the method further comprises advancing the access catheter into the contralateral femoral artery.

4. The method as in claim 1, wherein advancing the access wire comprises advancing through the contralateral iliofemoral artery, through the aorta and into the ipsilateral iliofemoral artery.

5. The method as in claim 4, wherein the access wire has sufficient stiffness to support advancement of the at least one treatment device through at least one bend in a blood vessel.

6. The method as in claim 1, further comprising, before inflating the balloon: injecting contrast into the ipsilateral artery; and
    observing the contrast using a radiographic imaging device to evaluate whether the vascular injury exists.

7. The method as in claim 1, wherein inflating the balloon comprises inflating at a location of the vascular injury.

8. The method as in claim 1, wherein inflating the balloon comprises inflating at a location upstream of the vascular injury.

9. The method as in claim 1, wherein the treatment device comprises a stent deployment catheter, and wherein treating the vascular injury comprises placing a stent in the blood vessel.

10. The method as in claim 1, wherein the intravascular procedure comprises implantation of an aortic valve.

11. The method as in claim 1, wherein the intravascular procedure comprises an abdominal aortic aneurysm repair.

12. The method of treating a vascular injury occurring during or after an intravascular procedure, the method comprising:
    advancing an access wire having an inflatable balloon integral to the wire through a previously placed access catheter in a first iliofemoral artery to position the inflatable balloon integral to the access wire in a vascular access sheath located in a second iliofemoral artery, without using any additional guidewires or catheters other than the access catheter to advance the access wire;
    locating the vascular injury in the second iliofemoral artery;
    inflating the balloon to occlude the second iliofemoral artery at or near the vascular injury;
    advancing at least one treatment device over a hubless proximal end of the access wire; and
    treating the vascular injury using the at least one treatment device.

13. A method of treating a vascular injury occurring during or after an intravascular procedure, the method comprising:
    advancing an access wire having an inflatable balloon integral to the wire through a previously placed access catheter in a first femoral artery to position the inflatable balloon integral to the access wire in a vascular access sheath located in a second femoral artery, without using any additional guidewires to advance the access wire;
    withdrawing the vascular access sheath at least partway out of the second femoral artery to expose the vascular injury;
    inflating the balloon within the vascular access sheath to anchor the access wire relative to the sheath;
    advancing at least one treatment device over a hubless proximal end of the access wire; and
    treating the vascular injury using the at least one treatment device.

* * * * *